United States Patent
He et al.

(10) Patent No.: US 11,365,425 B2
(45) Date of Patent: Jun. 21, 2022

(54) RESISTANT PROTEIN FOR USE IN HERBICIDE, ENCODING GENE AND APPLICATION THEREOF

(71) Applicants: BEIJING DABEINONG BIOTECHNOLOGY CO., LTD., Beijing (CN); NANJING AGRICULTURAL UNIVERSITY, Jiangsu (CN)

(72) Inventors: Jian He, Province (CN); Li Yao, Province (CN); Xingjun Jia, Province (CN); Xiangting Xie, Beijing (CN); Yechun Wu, Beijing (CN); Qing Tao, Beijing (CN); Derong Ding, Beijing (CN)

(73) Assignees: BEIJING DABEINONG BIOTECHNOLOGY CO., LTD., Beijing (CN); NANJING AGRICULTURAL UNIVERSITY, Jiangsu (CN)

( * ) Notice: Subject to any disclaimer, the term of this patent is extended or adjusted under 35 U.S.C. 154(b) by 358 days.

(21) Appl. No.: 16/308,852

(22) PCT Filed: Apr. 7, 2017

(86) PCT No.: PCT/CN2017/079661
§ 371 (c)(1),
(2) Date: Dec. 11, 2018

(87) PCT Pub. No.: WO2017/215329
PCT Pub. Date: Dec. 21, 2017

(65) Prior Publication Data
US 2019/0249187 A1    Aug. 15, 2019

(30) Foreign Application Priority Data
Jun. 18, 2016 (CN) .......................... 201610440763.7

(51) Int. Cl.
| | |
|---|---|
| *C12N 15/82* | (2006.01) |
| *C12N 5/10* | (2006.01) |
| *C12N 9/06* | (2006.01) |
| *C07K 14/415* | (2006.01) |
| *C12N 15/62* | (2006.01) |

(52) U.S. Cl.
CPC ........ *C12N 15/8274* (2013.01); *C07K 14/415* (2013.01); *C12N 5/10* (2013.01); *C12N 9/0028* (2013.01); *C12N 15/62* (2013.01); *C12N 15/82* (2013.01); *C12N 15/8201* (2013.01); *C12Y 105/0102* (2013.01)

(58) Field of Classification Search
CPC .......................... C12N 15/8274; C12N 9/0028
See application file for complete search history.

(56) References Cited

U.S. PATENT DOCUMENTS 7,022,896 B1 * 4/2006 Weeks .................. C12N 15/52
435/252.3

FOREIGN PATENT DOCUMENTS

| | | |
|---|---|---|
| CN | 101501196 | 8/2009 |
| CN | 102242133 A | 11/2011 |
| CN | 102776217 A | 11/2012 |
| CN | 105925590 A | 9/2016 |
| WO | WO-2007/146706 | 12/2007 |
| WO | WO-2008/095972 A1 | 8/2008 |

OTHER PUBLICATIONS

Yao, L 5, 10-methylene-THF reductase [*Sphingomonas* sp. Ndbn-20] Gen Bank Accession ALK02319.1 Published Oct. 26, 2015 (Year: 2015).*
GenBank Accession No. AY786443.1, *Stenotrophomonas maltophilia* strain DI-6 DdmC (ddmC) gene, complete cds, Jun. 29, 2005.
Hong et al., Methylene Tetrahydrofolate Reductase Regulates the Growth, Development and Pathogenicity of the Rice Blast Fungus Magnaporthe Oryzae, *Acta Phytopathologica Sinica*. 45:270-9 (2015).
International Preliminary Reporton Patentability, PCT/CN2017/079661 (dated Dec. 18, 2018).
International Search Report and Written Opinion, PCT/CN2017/079661 (dated Jul. 12, 2017).
Sheppard et al., Purification and properties of NADH-dependent 5, 10-methylenetetrahydrofolate reductase (MetF) from *Escherichia coli*, *Journal of Bacteriology*. 181:718-25 (1999).

* cited by examiner

*Primary Examiner* — David H Kruse
(74) *Attorney, Agent, or Firm* — Marshall, Gerstein & Borun LLP

(57) ABSTRACT

Provided are a resistant protein for use in herbicide dicamba, encoding gene and application thereof, the gene comprising: (a) a nucleotide sequence of an amino acid sequence as shown in SEQ ID NO: 2; or (b) a nucleotide sequence which is complementary to the nucleotide sequence as defined by (a) under stringent conditions; or (c) a nucleotide sequence as shown in SEQ ID NO: 1.

18 Claims, 12 Drawing Sheets
Specification includes a Sequence Listing.

A. Inactivated MTHFR66+1mM tetrahydrofolate (CK)

B. MTHFR66+1mM tetrahydrofolate (T)

A. MTHFR66+0.01mM tetrahydrofolate

B. MTHFR66+0.05mM tetrahydrofolate

C. MTHFR66+0.1mM tetrahydrofolate

D. MTHFR66+0.5mM tetrahydrofolate

E. MTHFR66+1mM tetrahydrofolate

A. 5-methyltetrahydrofolate (5-CH3-H4F) standard, the retention time was 7.02 min B. MTHFR66 + 5-CH3-H4F for 1 hour, the retention time of the intermediate product was 6.50 min A. Inactivated MTHFR66+5-CH$_3$-H$_4$F for 1 hour B. MTHFR66+5-CH$_3$-H$_4$F for 1 hour

Wild Type *Arabidopsis*  At-MTHFR66  At-mMTHFR66

SEQUENCE LISTING

```
<160> NUMBER OF SEQ ID NOS: 16

<210> SEQ ID NO 1
<211> LENGTH: 870
<212> TYPE: DNA
<213> ORGANISM: Artificial Sequence
<220> FEATURE:
<223> OTHER INFORMATION: The optimized MTHFR66 nucleotide sequence

<400> SEQUENCE: 1
atggggtccc ccgttatggc tattgattgc gactctgtgc cggataacct cgttcactgt        60
ttcagcatcg agatgaccgg caaggatata gacgcactgc aggcagctgc accactcctg       120
ccacctggaa catcagtcgc cgtgacgttt cttcctggcg agaattacga aactaggatt       180
gcggcctgca aagctgtgcg cgacttggga ttcgagccca tgccgcattt tagtgctagg       240
cgcatccagg atgaggcaga attccacgac tttctccatg cagtggttgc ggaagccaag       300
gtcagacggt gtttcgtgat cgctggagat gctgcagagc ccgaaggtcc gtatgcagac       360
agtatgcaac tcatagcttc gggggcattt gaggcggccg gcatagatct gattggtgtt       420
gccgggcacc cagaggggca tcctaacatg accgcgggcg aagctactgc agtccttcgc       480
```

```
gccaagacag acgagattga aaggcgcgga atggctgcat tgatcgtgac ccagttcact    540
tttgatgcgg ccagaacgct cgactggctg gcagaagtgc ggcaagcagg tatagatgtt    600
ccagtccttt tgggcgttcc aggacctgcc ggtattaaga cactcctgag attcgctgca    660
agatgcggtg ttggcgcttc cgcctctgtc ctcagcaaat acggaatttc aatcggtcac    720
cttttggggt ctgcaggacc agataggttc gtcgacgcac tgagggcagg aattggagag    780
caacacggcc atgtgaggct tcacttctac ccatttggcg gattggataa gacggctaga    840
tggatcgctg actatgcacg gaaacattga                                     870
```

<210> SEQ ID NO 2
<211> LENGTH: 289
<212> TYPE: PRT
<213> ORGANISM: Sphingomonas paucimobilis

<400> SEQUENCE: 2

```
Met Gly Ser Pro Val Met Ala Ile Asp Cys Asp Ser Val Pro Asp Asn
1               5                   10                  15

Leu Val His Cys Phe Ser Ile Glu Met Thr Gly Lys Asp Ile Asp Ala
            20                  25                  30

Leu Gln Ala Ala Pro Leu Leu Pro Pro Gly Thr Ser Val Ala Val
        35                  40                  45

Thr Phe Leu Pro Gly Glu Asn Tyr Glu Thr Arg Ile Ala Ala Cys Lys
50                  55                  60

Ala Val Arg Asp Leu Gly Phe Glu Pro Met Pro His Phe Ser Ala Arg
65                  70                  75                  80

Arg Ile Gln Asp Glu Ala Glu Phe His Asp Phe Leu His Ala Val Val
                85                  90                  95

Ala Glu Ala Lys Val Arg Arg Cys Phe Val Ile Ala Gly Asp Ala Ala
            100                 105                 110

Glu Pro Glu Gly Pro Tyr Ala Asp Ser Met Gln Leu Ile Ala Ser Gly
        115                 120                 125

Ala Phe Glu Ala Ala Gly Ile Asp Leu Ile Gly Val Ala Gly His Pro
130                 135                 140

Glu Gly His Pro Asn Met Thr Ala Gly Glu Ala Thr Ala Val Leu Arg
145                 150                 155                 160

Ala Lys Thr Asp Glu Ile Glu Arg Arg Gly Met Ala Ala Leu Ile Val
                165                 170                 175

Thr Gln Phe Thr Phe Asp Ala Ala Arg Thr Leu Asp Trp Leu Ala Glu
            180                 185                 190

Val Arg Gln Ala Gly Ile Asp Val Pro Val Leu Gly Val Pro Gly
        195                 200                 205

Pro Ala Gly Ile Lys Thr Leu Leu Arg Phe Ala Ala Arg Cys Gly Val
210                 215                 220

Gly Ala Ser Ala Ser Val Leu Ser Lys Tyr Gly Ile Ser Ile Gly His
225                 230                 235                 240

Leu Leu Gly Ser Ala Gly Pro Asp Arg Phe Val Asp Ala Leu Arg Ala
                245                 250                 255

Gly Ile Gly Glu Gln His Gly His Val Arg Leu His Phe Tyr Pro Phe
            260                 265                 270

Gly Gly Leu Asp Lys Thr Ala Arg Trp Ile Ala Asp Tyr Ala Arg Lys
        275                 280                 285

His
```

<210> SEQ ID NO 3
<211> LENGTH: 870
<212> TYPE: DNA
<213> ORGANISM: Sphingomonas paucimobilis

<400> SEQUENCE: 3

| | | | | | | |
|---|---|---|---|---|---|---|
| atgggctcgc | ccgttatggc | catcgattgc | gacagcgtgc | cggataatct | ggtgcattgc | 60 |
| ttctcgattg | agatgactgg | gaaggatatc | gatgcgctgc | aggcagcggc | gccgctcttg | 120 |
| ccccccggta | catccgtcgc | ggtgacgttc | ctgccaggcg | aaaactacga | gacgcggatc | 180 |
| gcagcctgca | aggcggtgcg | tgacctcggt | ttcgagccga | tgccgcattt | ctcagcccgt | 240 |
| cgcatccaag | acgaggcgga | gttccacgac | ttcctgcacg | ccgtcgtggc | tgaagccaag | 300 |
| gtgcggcgct | gcttcgtcat | cgccggagac | gccgctgagc | cggaaggccc | gtatgccgat | 360 |
| agcatgcagt | tgattgccag | cggcgccttt | gaggccgccg | ggatcgacct | gatcggcgtt | 420 |
| gcgggccatc | ccgaaggcca | tcccaacatg | acagcggggg | aggccaccgc | cgtcctgcgg | 480 |
| gccaagaccg | atgagatcga | aagacgcggt | atggcggcgc | tcatcgtcac | gcaatttacg | 540 |
| ttcgacgctg | cgcgcacgct | cgactggctc | gccgaagtac | gccaggccgg | catcgacgtc | 600 |
| ccggttctgc | tcggggtgcc | cggcccggcc | ggcatcaaga | cgcttttgcg | tttcgccgcg | 660 |
| cggtgcggcg | tcggcgcgtc | cgcatccgtg | ctgagcaaat | atggcatctc | gattggccat | 720 |
| ctgctcggat | cggccggccc | cgaccgcttc | gtcgatgcgc | tccgcgccgg | aattggcgaa | 780 |
| cagcatgggc | atgtccgcct | gcacttctac | cctttggcg | gcctcgacaa | acggcgcgg | 840 |
| tggatcgctg | actacgctcg | aaagcactga | | | | 870 |

<210> SEQ ID NO 4
<211> LENGTH: 29
<212> TYPE: DNA
<213> ORGANISM: Artificial Sequence
<220> FEATURE:
<223> OTHER INFORMATION: Primer 1

<400> SEQUENCE: 4
ggaattccat atgggctcgc ccgttatgg    29

<210> SEQ ID NO 5
<211> LENGTH: 29
<212> TYPE: DNA
<213> ORGANISM: Artificial Sequence
<220> FEATURE:
<223> OTHER INFORMATION: Primer 2

<400> SEQUENCE: 5
ccgctcgagg tgctttcgag cgtagtcag    29

<210> SEQ ID NO 6
<211> LENGTH: 1322
<212> TYPE: DNA
<213> ORGANISM: Arabidopsis thaliana

<400> SEQUENCE: 6

| | | | | | | |
|---|---|---|---|---|---|---|
| gtcgacctgc | aggtcaacgg | atcaggatat | tcttgtttaa | gatgttgaac | tctatggagg | 60 |
| tttgtatgaa | ctgatgatct | aggaccggat | aagttcccct | cttcatagcg | aacttattca | 120 |
| aagaatgttt | tgtgtatcat | tcttgttaca | ttgttattaa | tgaaaaaata | ttattggtca | 180 |
| ttggactgaa | cacgagtgtt | aaatatggac | caggccccaa | ataagatcca | ttgatatatg | 240 |
| aattaaataa | caagaataaa | tcgagtcacc | aaaccacttg | cctttttaa | cgagacttgt | 300 |

```
tcaccaactt gatacaaaag tcattatcct atgcaaatca ataatcatac aaaaatatcc    360
aataacacta aaaaattaaa agaaatggat aatttcacaa tatgttatac gataaagaag    420
ttacttttcc aagaaattca ctgattttat aagcccactt gcattagata aatggcaaaa    480
aaaaacaaaa aggaaaagaa ataaagcacg aagaattcta gaaaatacga aatacgcttc    540
aatgcagtgg gacccacggt tcaattattg ccaattttca gctccaccgt atatttaaaa    600
aataaaacga taatgctaaa aaatataaa tcgtaacgat cgttaaatct caacggctgg    660
atcttatgac gaccgttaga aattgtggtt gtcgacgagt cagtaataaa cggcgtcaaa    720
gtggttgcag ccggcacaca cgagtcgtgt ttatcaactc aaagcacaaa tacttttcct    780
caacctaaaa ataaggcaat tagccaaaaa caactttgcg tgtaaacaac gctcaataca    840
cgtgtcattt tattattagc tattgcttca ccgccttagc tttctcgtga cctagtcgtc    900
ctcgtctttt cttcttcttc ttctataaaa caatacccaa agcttcttct tcacaattca    960
gatttcaatt tctcaaaatc ttaaaaactt tctctcaatt ctctctaccg tgatcaaggt   1020
aaatttctgt gttccttatt ctctcaaaat cttcgatttt gttttcgttc gatcccaatt   1080
tcgtatatgt tctttggttt agattctgtt aatcttagat cgaagacgat tttctgggtt   1140
tgatcgttag atatcatctt aattctcgat tagggtttca taaatatcat ccgatttgtt   1200
caaataattt gagttttgtc gaataattac tcttcgattt gtgatttcta tctagatctg   1260
gtgttagttt ctagtttgtg cgatcgaatt tgtcgattaa tctgagtttt tctgattaac   1320
ag                                                                 1322
```

```
<210> SEQ ID NO 7
<211> LENGTH: 228
<212> TYPE: DNA
<213> ORGANISM: Arabidopsis thaliana

<400> SEQUENCE: 7
atggcgcaag ttagcagaat ctgcaatggt gtgcagaacc catctcttat ctccaatctc     60
tcgaaatcca gtcaacgcaa atctccctta tcggtttctc tgaagacgca gcagcatcca    120
cgagcttatc cgatttcgtc gtcgtgggga ttgaagaaga gtgggatgac gttaattggc    180
tctgagcttc gtcctcttaa ggtcatgtct tctgtttcca cggcgtgc                 228

<210> SEQ ID NO 8
<211> LENGTH: 253
<212> TYPE: DNA
<213> ORGANISM: Agrobacterium tumefaciens

<400> SEQUENCE: 8
gatcgttcaa acatttggca ataaagtttc ttaagattga atcctgttgc cggtcttgcg     60
atgattatca tataatttct gttgaattac gttaagcatg taataattaa catgtaatgc    120
atgacgttat ttatgagatg ggttttatg attagagtcc cgcaattata catttaatac    180
gcgatagaaa acaaaatata gcgcgcaaac taggataaat tatcgcgcgc ggtgtcatct    240
atgttactag atc                                                      253

<210> SEQ ID NO 9
<211> LENGTH: 530
<212> TYPE: DNA
<213> ORGANISM: Cauliflower mosaic virus

<400> SEQUENCE: 9
```

| | |
|---|---|
| ccatggagtc aaagattcaa atagaggacc taacagaact cgccgtaaag actggcgaac | 60 |
| agttcataca gagtctctta cgactcaatg acaagaagaa atcttcgtc aacatggtgg | 120 |
| agcacgacac gcttgtctac tccaaaaata tcaaagatac agtctcagaa gaccaaaggg | 180 |
| caattgagac ttttcaacaa agggtaatat ccggaaacct cctcggattc cattgcccag | 240 |
| ctatctgtca ctttattgtg aagatagtgg aaaaggaagg tggctcctac aaatgccatc | 300 |
| attgcgataa aggaaaggcc atcgttgaag atgcctctgc cgacagtggt cccaaagatg | 360 |
| gaccccacc cacgaggagc atcgtggaaa agaagacgt tccaaccacg tcttcaaagc | 420 |
| aagtggattg atgtgatatc tccactgacg taagggatga cgcacaatcc cactatcctt | 480 |
| cgcaagaccc ttcctctata taaggaagtt catttcattt ggagaggaca | 530 |

<210> SEQ ID NO 10
<211> LENGTH: 552
<212> TYPE: DNA
<213> ORGANISM: Streptomyces viridochromogenes

<400> SEQUENCE: 10

| | |
|---|---|
| atgtctccgg agaggagacc agttgagatt aggccagcta cagcagctga tatggccgcg | 60 |
| gtttgtgata tcgttaacca ttacattgag acgtctacag tgaactttag acagagcca | 120 |
| caaacaccac aagagtggat tgatgatcta gagaggttgc aagatagata cccttggttg | 180 |
| gttgctgagg ttgagggtgt tgtggctggt attgcttacg ctgggccctg aaggctagg | 240 |
| aacgcttacg attggacagt tgagagtact gtttacgtgt cacataggca tcaaaggttg | 300 |
| ggcctaggat ccacattgta cacacatttg cttaagtcta tggaggcgca aggttttaag | 360 |
| tctgtggttg ctgttatagg ccttccaaac gatccatctg ttaggttgca tgaggctttg | 420 |
| ggatacacag cccggggtac attgcgcgca gctggataca agcatggtgg atggcatgat | 480 |
| gttggttttt ggcaaaggga ttttgagttg ccagctcctc caaggccagt taggccagtt | 540 |
| acccagatct ga | 552 |

<210> SEQ ID NO 11
<211> LENGTH: 195
<212> TYPE: DNA
<213> ORGANISM: Cauliflower mosaic virus

<400> SEQUENCE: 11

| | |
|---|---|
| ctgaaatcac cagtctctct ctacaaatct atctctctct ataataatgt gtgagtagtt | 60 |
| cccagataag ggaattaggg ttcttatagg gtttcgctca tgtgttgagc atataagaaa | 120 |
| cccttagtat gtatttgtat ttgtaaaata cttctatcaa taaaatttct aattcctaaa | 180 |
| accaaaatcc agtgg | 195 |

<210> SEQ ID NO 12
<211> LENGTH: 1992
<212> TYPE: DNA
<213> ORGANISM: Zea mays

<400> SEQUENCE: 12

| | |
|---|---|
| ctgcagtgca gcgtgacccg tcgtgccccc tctctagaga taatgagcat tgcatgtcta | 60 |
| agttataaaa aattaccaca tattttttt gtcacacttg tttgaagtgc agtttatcta | 120 |
| tctttataca tatatttaaa ctttactcta cgaataatat aatctatagt actacaataa | 180 |
| tatcagtgtt ttagagaatc atataaatga acagttagac atggtctaaa ggacaattga | 240 |
| gtattttgac aacaggactc tacagtttta tcttttagt gtgcatgtgt tctccttttt | 300 |

-continued

```
ttttgcaaat agcttcacct atataatact tcatccattt tattagtaca tccatttagg    360
gtttagggtt aatggttttt atagactaat ttttttagta catctatttt attctatttt    420
agcctctaaa ttaagaaaac taaaactcta ttttagtttt tttatttaat aatttagata    480
taaaatagaa taaaataaag tgactaaaaa ttaaacaaat acccctttaag aaattaaaaa   540 aactaaggaa acattttttct tgtttcgagt agataatgcc agcctgttaa acgccgtcga    600
cgagtctaac ggacaccaac cagcgaacca gcagcgtcgc gtcgggccaa gcgaagcaga    660
cggcacggca tctctgtcgc tgcctctgga cccctctcga gagttccgct ccaccgttgg    720
acttgctccg ctgtcggcat ccagaaattg cgtggcggag cggcagacgt gagccggcac    780
ggcaggcggc ctcctcctcc tctcacggca cggcagctac gggggattcc tttcccaccg    840
ctccttcgct ttcccttcct cgcccgccgt aataaataga caccccctcc cacccctctt    900
tccccaacct cgtgttgttc ggagcgcaca cacacacaac cagatctccc ccaaatccac    960
ccgtcggcac ctccgcttca aggtacgccg ctcgtcctcc ccccccccc ctctctacct    1020 tctctagatc ggcgttccgg tccatggtta gggcccggta gttctacttc tgttcatgtt    1080
tgtgttagat ccgtgtttgt gttagatccg tgctgctagc gttcgtacac ggatgcgacc    1140
tgtacgtcag acacgttctg attgctaact tgccagtgtt tctctttggg gaatcctggg    1200
atggctctag ccgttccgca gacgggatcg atttcatgat ttttttttgtt tcgttgcata    1260 gggtttggtt tgccctttc ctttatttca atatatgccg tgcacttgtt tgtcgggtca    1320
tcttttcatg ctttttttttg tcttggttgt gatgatgtgg tctggttggg cggtcgttct    1380
agatcggagt agaattctgt ttcaaactac ctggtggatt tattaatttt ggatctgtat    1440
gtgtgtgcca tacatattca tagttacgaa ttgaagatga tggatggaaa tatcgatcta    1500
ggataggtat acatgttgat gcgggtttta ctgatgcata tacagagatg cttttttgttc    1560 gcttggttgt gatgatgtgg tgtgttgggg cggtcgttca ttcgttctag atcggagtag    1620
aatactgttt caaactacct ggtgtattta ttaattttgg aactgtatgt gtgtgtcata    1680
catcttcata gttacgagtt taagatggat ggaaatatcg atctaggata ggtatacatg    1740
ttgatgtggg ttttactgat gcatatacat gatggcatat gcagcatcta ttcatatgct    1800
ctaaccttga gtacctatct attataataa acaagtatgt tttataatta ttttgatctt    1860
gatatacttg gatgatggca tatgcagcag ctatatgtgg attttttttag ccctgccttc    1920 atacgctatt tatttgcttg gtactgtttc ttttgtcgat gctcaccctg ttgtttggtg    1980
ttacttctgc ag                                                       1992
```

```
<210> SEQ ID NO 13
<211> LENGTH: 1176
<212> TYPE: DNA
<213> ORGANISM: Escherichia coli

<400> SEQUENCE: 13
```

```
atgcaaaaac tcattaactc agtgcaaaac tatgcctggg gcagcaaaac ggcgttgact    60
gaactttatg gtatggaaaa tccgtccagc cagccgatgg ccgagctgtg gatgggcgca   120
catccgaaaa gcagttcacg agtgcagaat gccgccggag atatcgtttc actgcgtgat    180
gtgattgaga gtgataaatc gactctgctc ggagaggccg ttgccaaacg ctttggcgaa    240
ctgcctttcc tgttcaaagt attatgcgca gcacagccac tctccattca ggttcatcca    300
aacaaacaca attctgaaat cggttttgcc aaagaaaatg ccgcaggtat cccgatggat    360
```

```
gccgccgagc gtaactataa agatcctaac cacaagccgg agctggtttt tgcgctgacg        420
cctttccttg cgatgaacgc gtttcgtgaa ttttccgaga ttgtctccct actccagccg        480
gtcgcaggtg cacatccggc gattgctcac tttttacaac agcctgatgc cgaacgttta        540
agcgaactgt tcgccagcct gttgaatatg cagggtgaag aaaaatcccg cgcgctggcg        600
attttaaaat cggccctcga tagccagcag ggtgaaccgt ggcaaacgat tcgtttaatt        660 tctgaattt acccggaaga cagcggtctg ttctccccgc tattgctgaa tgtggtgaaa         720
ttgaaccctg gcgaagcgat gttcctgttc gctgaaacac cgcacgctta cctgcaaggc        780
gtggcgctgg aagtgatggc aaactccgat aacgtgctgc gtgcgggtct gacgcctaaa        840
tacattgata ttccggaact ggttgccaat gtgaaattcg aagccaaacc ggctaaccag        900
ttgttgaccc agccggtgaa acaaggtgca gaactggact tcccgattcc agtggatgat        960
tttgccttct cgctgcatga ccttagtgat aaagaaacca ccattagcca gcagagtgcc       1020
gccattttgt tctgcgtcga aggcgatgca acgttgtgga aggttctca gcagttacag        1080 cttaaaccgg gtgaatcagc gtttattgcc gccaacgaat caccggtgac tgtcaaaggc       1140
cacggccgtt tagcgcgtgt ttacaacaag ctgtaa                                  1176
```

```
<210> SEQ ID NO 14
<211> LENGTH: 18
<212> TYPE: DNA
<213> ORGANISM: Artificial Sequence
<220> FEATURE:
<223> OTHER INFORMATION: Primer 3

<400> SEQUENCE: 14
ccgggtgaat cagcgttt                                                       18

<210> SEQ ID NO 15
<211> LENGTH: 18
<212> TYPE: DNA
<213> ORGANISM: Artificial Sequence
<220> FEATURE:
<223> OTHER INFORMATION: Primer 4

<400> SEQUENCE: 15
gccgtggcct ttgacagt                                                       18

<210> SEQ ID NO 16
<211> LENGTH: 20
<212> TYPE: DNA
<213> ORGANISM: Artificial Sequence
<220> FEATURE:
<223> OTHER INFORMATION: Probe 1

<400> SEQUENCE: 16
tgccgccaac gaatcaccgg                                                     20
```

RESISTANT PROTEIN FOR USE IN HERBICIDE, ENCODING GENE AND APPLICATION THEREOF

TECHNICAL FIELD

The present invention relates to a herbicide resistant protein, a coding gene thereof and use thereof, and in particular to a protein tolerant to herbicide dicamba, a coding gene thereof and use thereof.

BACKGROUND

Weeds may exhaust valuable nutrients required by crops and other plants of interest in the soil rapidly. Despite that at present, transgenic plants tolerant to the treatment of herbicides, such as glyphosate, glufosinate, 2,4-D and the like can be available, there is still a blank area, such as the range of controlled weeds, and development of the crops tolerant to additional herbicides. In addition, the emergence of weeds tolerant to the above-mentioned herbicides (despite that they are usually local and variable) gives rise to needs of additional or alternative weed control measures.

It is proven that herbicide tolerance traits are commercially valuable, and therefore it is necessary to increase the plants tolerant to other herbicides and manage options of weeds species which are difficult to be controlled, in order to avoid overdependence on any single herbicide. In particular, it is necessary to develop herbicide tolerance to environment-friendly herbicides highly effective in terms of weed control. As one of the effective and environmentally friendly herbicides, dicamba has been used by farmers for 40 years, and can be used to control annual and perennial broad-leafed weeds and a few narrow-leafed weeds in maize, sorghum, millet, forage grass, hay, pasture, sugar cane, asparagus, turf and grass seed crops; and at the same time, dicamba can damage many commercial crops and dicotyledonous plants, such as soybean, cotton, pea, potato, sunflower and oilseed rape, and the crops/plants as mentioned above are particularly sensitive to low-level dicamba. Nevertheless, dicamba is still effective and important in controlling weed growth.

It has been reported that a gene encoding dicamba monooxygenase (DMO) is separated from *Pseudomonas maltophilia*, the monooxygenase being ferredoxin-dependent and conferring dicamba tolerance. DMO participates in transforming herbicide dicamba (3,6-dichloro-o-anisic acid) to non-toxic 3,6-dichlorosalicylic acid (DCSA), and thus a plant expressing DMO gene has tolerance to dicamba.

Because dicamba tolerant genes found so far are very similar, more novel dicamba tolerant genes are required to avoid over-dependence on one dicamba tolerant gene, so that dicamba-dicamba tolerant crops have a broader application space commercially.

SUMMARY OF THE INVENTION

An objective of the present invention is to provide a herbicide resistant protein, a coding gene thereof and use thereof. The MTHFR66 protein has higher tolerance to a dicamba herbicide in plants.

In order to achieve the above objective, the present invention provides a gene, comprising:
(a) a nucleotide sequence encoding the amino acid sequence shown as SEQ ID NO: 2; or
(b) a nucleotide sequence complementary to the nucleotide sequence defined in (a) under stringent conditions; or
(c) a nucleotide sequence shown as SEQ ID NO: 1.

The stringent conditions can be hybridization in a solution of 6×SSC (sodium citrate) and 0.5% SDS (lauryl sodium sulfate) at 65° C., and then washing the membrane once with 2×SSC, 0.1% SDS, and 1×SSC, 0.1% SDS respectively.

In order to achieve the above objective, the present invention further provides an expression cassette comprising the gene under the regulation of an effectively linked regulatory sequence.

Furthermore, the regulatory sequence is a chloroplast transit peptide effectively linked to the gene.

Preferably, the nucleotide sequence of the chloroplast transit peptide is a nucleotide sequence shown as SEQ ID NO: 7.

In order to achieve the above objective, the present invention also provides a recombinant vector containing the gene or the expression cassette.

In order to achieve the above objective, the present invention also provides a method for increasing the herbicide tolerance ranges, comprising: expressing the protein consisting of the amino acid sequence shown as SEQ ID NO: 2 or the protein encoded by the expression cassette in a plant together with at least one second protein which is different from the protein consisting of the amino acid sequence shown as SEQ ID NO: 2 or the protein encoded by the expression cassette.

Further, the second protein is a glyphosate tolerant protein, a glufosinate tolerant protein, α-ketoglutarate dioxygenase, 4-hydroxyphenylpyruvate dioxygenase, acetolactate synthase, cytochrome-like proteins or protoporphyrinogen oxidase.

In the present invention, the expression of the herbicide resistant MTHFR66 protein in a transgenic plant can be accompanied by the expression of one or more glyphosate tolerant proteins and/or glufosinate tolerant proteins. This co-expression of more than one herbicide tolerant protein in the same transgenic plant can be achieved by allowing the plant to comprise and express a desired gene through genetic engineering. In addition, a plant (a first parent) can express the herbicide resistant MTHFR66 protein through genetic engineering manipulation, and a second plant (a second parent) can express a glyphosate tolerant protein and/or glufosinate tolerant protein through genetic engineering manipulation. Progeny plants expressing all the genes introduced into the first parent and the second parent are obtained by hybridizing the first parent with the second parent.

In order to achieve the above objective, the present invention also provides a method for selecting transformed plant cells, comprising: transforming a plurality of plant cells with the gene or the expression cassette, and cultivating the cells under a concentration of herbicide allowing the growth of the transformed cells expressing the gene or the expression cassette, while killing the untransformed cells or inhibiting the growth of the untransformed cells, wherein the herbicide is dicamba.

In order to achieve the above objective, the present invention also provides a method for controlling weeds, comprising: applying an effective dose of a dicamba herbicide to a field for planting a plant, the plant containing the gene, the expression cassette or the recombinant vector.

In order to achieve the above objective, the present invention also provides a method for protecting a plant from damages caused by the herbicides, comprising: introducing the gene, the expression cassette or the recombinant vector into a plant to make the post-introduction plant produce a sufficient amount of herbicide tolerant proteins for protecting the plant from damages caused by dicamba.

In order to achieve the above objective, the present invention also provides a method for imparting dicamba herbicide tolerance to a plant, comprising: introducing the gene, the expression cassette or the recombinant vector into the plant.

In order to achieve the above objective, the present invention also provides a method for controlling glyphosate tolerant weeds in a field for a glyphosate tolerant plant, comprising: applying an effective dose of dicamba to a field for planting a glyphosate tolerant plant, the glyphosate tolerant plant containing the gene, the expression cassette or the recombinant vector.

In order to achieve the above objective, the present invention also provides a method for producing a dicamba tolerant plant, comprising introducing the gene or the expression cassette into the genome of the plant to produce the dicamba tolerant plant.

Specifically, the method for producing a dicamba tolerant plant comprises: producing a dicamba tolerant plant by selfing of a parent plant or hybridizing a parent plant with a second plant, the parent plant and/or the second plant containing the gene or the expression cassette, and the dicamba tolerant plant inheriting the gene or the expression cassette from the parent plant and/or the second plant.

In order to achieve the above objective, the present invention also provides a method for cultivating a plant tolerant to a dicamba herbicide, comprising:

planting at least one plant seed, the genome of which
  containing the gene or the expression cassette;
growing the plant seed into a plant;
and spraying the plant with an effective dose of the dicamba
  herbicide, and harvesting a plant having a reduced plant
  damage compared to other plants without the gene or the
  expression cassette.

On the basis of the above-mentioned technical solution, preferably, the plant is soybean, cotton, maize, rice, wheat, beet or sugar cane.

In order to achieve the above objective, the present invention further provides the use of methyltetrahydrofolate reductase in tolerating to a dicamba herbicide, wherein the methyltetrahydrofolate reductase has an amino acid sequence shown as SEQ ID NO: 2.

In order to achieve the above objective, the present invention further provides the use of a plant producing methyltetrahydrofolate reductase in tolerating to a dicamba herbicide, wherein the methyltetrahydrofolate reductase has an amino acid sequence shown as SEQ ID NO: 2.

The gene or the expression cassette or the recombinant vector is introduced into a plant. In order to introduce the exogenous DNA into plant cells in the present invention, the conventional transformation methods include, but are not limited to, the *Agrobacterium*-mediated transformation, microprojectile bombardment, direct uptake of DNA into the protoplast, electroporation or silicon whisker-mediated DNA introduction.

The present invention can increase plant tolerance to oxidative stress, including but not limited to, providing a flora with metabolites or the like mediated by dicamba or dicamba monooxygenase to improve herbicide tolerance of plants by, for example, metabolizing dicamba to DCSA.

The "dicamba" in the present invention refers to 3,6-dichloro-o-anisic acid or 3,6-dichloro-2-methoxybenzoic acid and acids and salts thereof, in which the salts thereof include isopropylamine salt, diglycolamine salt, dimethylamine salt, potassium salt and sodium salt. Commercial preparations of dicamba include, but are not limited to, Banvel® (as a DMA salt), Clarity® (BASF, as a DGA salt), VEL-58-CS-11™ and Vanquish® (BASF, as a DGA salt).

At present, four demethylases of methoxyaromatic compounds have been reported, which are respectively: (1) RHOs (Rieske non-heme oxidase): DMO degrading dicamba (GenBank: AY786443.1) belonging to a tricomponent RHO oxidase; (2) cytochrome P450: it belongs to a superfamily of heme-thiolate proteins, and participates in metabolism of endogenous substances and exogenous substances including drugs and environmental compounds. Many demethylases of methoxyaromatic compounds belong to this type; (3) anaerobic tetrahydrofolate-dependent demethylase: it is found in anaerobic bacteria such as *Moorellathermoacetica*, and participates in anaerobic degradation of lignin degradation intermediate products such as syringic acid and vanillic acid. Some researches found that anaerobic tetrahydrofolate-dependent demethylase can also anaerobically degrade dicamba; and (4) aerobic tetrahydrofolate-dependent demethylase (*Sphingomonas paucimobilis* SYK-6): it participates in anaerobic degradation of lignin degradation intermediate products such as syringic acid and vanillic acid, but at present, there is no report that such aerobic tetrahydrofolate-dependent demethylases can degrade dicamba.

MTHFR is 5,10-methylenetetrahydrofolate reductase protein coding gene, and mainly plays a role in transforming 5,10-methylenetetrahydrofolate to 5-methyltetrahydrofolate having a biological function and the reverse reaction thereof in the folate metabolic pathway.

The gene of the present invention has the characteristic of allowing the use of a dicamba herbicide in plants after being used for the expression in the plants, wherein the absence or lack of inherent tolerance in the plants does not allow the use of the dicamba herbicide. In addition, the MTHFR66 gene of the present invention can provide protection against a dicamba herbicide in plants when the natural tolerance of plants is insufficient for selectivity. The application amount of dicamba to a field is about 0.0025 pounds/acre (lb/a) to about 20 lb/a, and more usually 0.25 lb/a to 12 lb/a. Combination of herbicides with various chemical categories and different modes and ranges of actions in the same field (continuously or in a tank-mixed combination) can provide control for most potential weeds needing to be controlled by the herbicides.

Glyphosate is widely used, as it controls a very broad spectrum of broad-leaved and gramineous weed species. However, reusing glyphosate in glyphosate tolerant crops and non-crop applications has been (and still will be) chosen to make weeds evolve into naturally more tolerant species or glyphosate tolerant biotypes. Most herbicide tolerance management strategies suggest using an effective amount of tank-mixed herbicide partners as a means of delaying the emergence of tolerant weeds, wherein the herbicide partners provide control of the same species, but have different modes of action. Superposing the MTHFR66 gene with a glyphosate tolerance trait (and/or another herbicide tolerance trait) can achieve control of glyphosate tolerant weed species (broad-leaved weed species controlled by dicamba) in glyphosate tolerant crops by allowing for selective use of glyphosate and dicamba on the same crop. The application of these herbicides can be performed by using simultaneously in a tank mixture containing two or more herbicides with different modes of action, or using a single herbicide composition alone in continuous use (e.g., before planting, before or after emergence) (with an interval time range used being from 2 hours to 3 months), or alternatively, can be performed by using a combination of any number of herbicides representative of each applicable compound category at any time (from 7 months after planting a crop to the time when the crop is harvested (or the pre-harvest interval for a single herbicide, taking the shortest)).

The flexibility in controlling broad-leaved weeds is very important, i.e., application time, single application amount of herbicide, and abilities for controlling the stubborn or tolerant weeds. The application range of glyphosate superposed with a glyphosate tolerant gene/MTHFR66 gene in crops can be from 250 to 2500 g ae/ha; and that of dicamba can be from 0.25 lb/a to 12 lb/a. The optimal combination of time for these applications depends on the specific conditions, species and environments.

A herbicide preparation (e.g., an ester, acid or salt-formulated or soluble concentrate, emulsifying concentrate or soluble liquid) and a tank mix additive (e.g., an adjuvant or compatilizer) can significantly affect weed control of a given herbicide or a combination of one or more herbicides. Any chemical combination of any of the foregoing herbicides is within the scope of the present invention.

It is well known for a person skilled in the art that the benefits of a combination of two or more modes of action in improving the controlled spectrum of weed and/or natural more tolerant species or tolerant weed species can also be extended to artificial (transgenosis or non-transgenosis) production of herbicide tolerant chemicals in addition to glyphosate tolerant crops in crops. In fact, the following tolerant traits can be encoded by a single or a multiple combination of superposition to effectively control or prevent the succession of weeds from developing tolerance to any of the above categories of herbicides. Glyphosate tolerance (e.g. tolerant plant or bacterial EPSPS, GOX, GAT), glufosinate tolerance (e.g. PAT, Bar), tolerance to phenoxy auxin (e.g., 2,4-D, 2-methyl-4-chlorophenoxy acetic acid tolerant genes, such as AAD-1, AAD-12, etc.), tolerance to herbicide inhibiting acetolactate synthase (ALS) (e.g. genes tolerant to imidazolinone, sulfonylurea, triazolopyrimidine, sulphonanilide, pyrimidinyl-thiobenzoic acid and other chemicals, such as AHAS, Csrl, SurA, etc.), bromoxynil tolerance (e.g. Bxn), tolerance to HPPD (4-hydroxyphenyl pyruvate dioxygenase) inhibitor, tolerance to phytoene desaturase (PDS) inhibitor, tolerance to herbicide inhibiting photosystem II (e.g. psbA), tolerance to herbicide inhibiting photosystem I, tolerance to herbicide inhibiting protoporphyrinogen oxidase IX (PPO) (e.g. PPO-1), phenylurea herbicide tolerance (e.g. CYP76B1), dichloromethoxyl benzoic acid degrading enzyme and so on.

As regards other herbicides, some other preferred ALS inhibitors include triazolopyrimidinyl sulphonanilide (cloransulam-methyl, diclosulam, flumetsulam, metosulam and penoxsulam), pyrmidinyl-thiobenzoic acid and flucarbazone. Some preferred HPPD inhibitors include mesotrione, isoxaflutole and sulcotrione. Some preferred PPO inhibitors include flumioxazin, butafenacil, carfentrazone, sulfentrazone and diphenyl ether (such as acifluorfen, fomesafen, lactofen and oxyfluorfen).

In addition, the MTHFR66 gene alone or the MTHFR66 gene superposed with other characteristics of herbicide resistant crops can be superposed with one or more other introduced traits (for example insect tolerance, fungal tolerance or stress tolerance, etc.) or exported traits (for example increased yield, improved oil amount, increased fiber quality, etc.). Therefore, the present invention can be used to provide abilities for flexibly and economically controlling any number of agriculture pests and complete agricultural solutions for improving qualities of crops.

The MTHFR66 gene of the present invention can degrade a dicamba herbicide, and is an important basis of herbicide tolerant crops and the possibility for selecting marker features.

Transgenic expression can be performed in the present invention, and almost all combinations of herbicides for broad-leaved weeds can be controlled. The MTHFR66 gene as an excellent trait of herbicide tolerant crops can be superposed with, for example, other traits of herbicide tolerant crops (for example, glyphosate tolerance, glufosinate tolerance, tolerance to phenoxy auxin, tolerance to ALS inhibitor (for example, imidazolinones, sulfonylureas, triazolopyrimidinyl sulfonamides), bromoxynil tolerance, HPPD inhibitor tolerance, PPO inhibitor tolerance, and the like) and traits of insect tolerance (Cry1Ab, Cry1F, Vip3, other *Bacillus thuringiensis* proteins or insect tolerant proteins derived from non-bacillus bacterial species, etc.). In addition, the MTHFR66 gene can be used as a selective marker for the assistant selection of primary transformants of plants genetically modified with another gene or gene group.

The traits of herbicide tolerant crops of the present invention can be used in a new combination with other traits (including but not limited to glyphosate tolerance) of herbicide tolerant crops. A new method for controlling the weed species can be produced by the combination of these traits due to newly obtained tolerance or inherent tolerance to a herbicide (for example glyphosate). Therefore, apart from the traits of herbicide tolerant crops, the scope of the present invention includes the new method for controlling weeds with herbicides, wherein the tolerance to the herbicides can be produced by the enzyme in the transgenic crops.

The present invention may be applied to a variety of plants, such as *Arabidopsis thaliana*, tobacco, soybean, cotton, rice, maize and *Brassica*. The present invention may also be used in a variety of other monocotyledonous crops (such as gramineous forage grass or gramineous turf grass) and dicotyledonous crops (such as alfalfa, clover, arbor species, etc.). Similarly, dicamba (or other MTHFR66 substrates) of the present invention can be more actively used in gramineous crops with moderate tolerance, and thus the improved tolerance obtained by such traits can provide planters a possibility of using these herbicides with a more effective application amount and a broader application time without crop damage risks.

The genome of a plant, plant tissue or plant cell in the present invention refers to any genetic material within the plant, plant tissue or plant cell, and includes nuclear, plastid and mitochondrial genomes.

The "tolerance" and the "resistance" in the present invention are heritable, and allows a plant to grow and propagate in the case where an effective treatment by a general herbicide is performed on a given plant. As recognized by a person skilled in the art, even if a certain damage degree of a plant treated with a herbicide is apparent, the plant can still be considered "tolerant" or "resistant". The term "tolerance" in the present invention is more extensive than the term "resistance", and includes "resistance" and an improved ability of a particular plant to resist various degrees of damage induced by a herbicide, and generally damages to a wild-type plant with the same genotype can be caused at the same herbicide dose.

The polynucleotide and/or nucleotide in the present invention forms a complete "gene", which encodes a protein or a polypeptide in a desired host cell. A person skilled in the art will be readily appreciated that the polynucleotide and/or nucleotide in the present invention can be placed under the control of a regulatory sequence in a host of interest.

The regulatory sequence in the present invention includes, but is not limited to, a promoter, a transit peptide, a terminator, an enhancer, a leader sequence, an intron and other regulatory sequences operably linked to the MTHFR66 gene.

The promoter is a plant expressible promoter. The "plant expressible promoter" refers to a promoter that ensures the expression of the coding sequence linked thereto in a plant cell. The plant expressible promoter can be a constitutive promoter. Examples of the promoters directing the constitutive expression in plants include, but are not limited to, 35S promoter derived from cauliflower mosaic virus, maize ubi promoters, rice GOS2 gene promoters, and the like. Alternatively, the plant expressible promoter can be a tissue specific promoter, i.e. the promoter directs the expression of an coding sequence in several tissues such as green tissues at a level higher than in other tissues of the plant (which can be measured through conventional RNA trials), such as a PEP carboxylase promoter. Alternatively, the plant expressible promoter can be a wound-inducible promoter. The wound-inducible promoter or a promoter directing a wound-induced expression pattern means that when a plant suffers from wound caused by a mechanical factor or gnawing of insects, the expression of the coding sequence under the regulation of the promoter is significantly improved than under normal growth conditions. Examples of the wound-inducible promoters include, but are not limited to, promoters of potato and tomato protease inhibitor genes (pin I and pin II) and maize protease inhibitor gene (MPI).

The transit peptide (also known as secretion signal sequence or targeting sequence) directs a transgenic product to a specific organelle or cell compartment. For a receptor protein, the transit peptide may be heterologous, for example, targeting the chloroplast using a sequence encoding the chloroplast transit peptide, including but not limited to *Arabidopsis thaliana* chloroplast transit peptide AtCTP2, or targeting the endoplasmic reticulum using a 'KDEL' retention sequence, or targeting the vacuole using CTPP of the barley phytolectin gene.

The leader sequence includes, but is not limited to, a small RNA virus leader sequence, such as EMCV leader sequence (5' non-coding region of encephlomyocarditis virus); a potato virus Y group leader sequence, such as MDMV (Maize Dwarf Mosaic Virus) leader sequence; human immunoglobulin heavy chain binding protein (BiP); an untranslated leader sequence of the coat protein mRNA of alfalfa mosaic virus (AMV RNA4); and a tobacco mosaic virus (TMV) leader sequence.

The enhancer includes, but is not limited to, cauliflower mosaic virus (CaMV) enhancer, figwort mosaic virus (FMV) enhancer, carnation etched ring virus (CERV) enhancer, cassava vein mosaic virus (CsVMV) enhancer, mirabilis mosaic virus (MMV) enhancer, cestrum yellow leaf curling virus (CmYLCV) enhancer, cotton leaf curl Multan virus (CLCuMV) enhancer, commelina yellow mottle virus (CoYMV) enhancer and peanut chloroticstreak caulimovirus (PCLSV) enhancer.

For use in a monocotyledonous plant, the intron includes, but is not limited to, maize hsp70 intron, maize ubiquitin intron, Adh intron 1, sucrose synthase intron or rice Act1 intron. For use in a dicotyledonous plant, the intron includes, but is not limited to, CAT-1 intron, pKANNIBAL intron, PIV2 intron and "super ubiquitin" intron.

The terminator can be a suitable polyadenylation signal sequence that functions in a plant, including, but not limited to, a polyadenylation signal sequence derived from the *Agrobacterium tumefaciens* nopaline synthetase (NOS) gene, a polyadenylation signal sequence derived from the protease inhibitor II (pinII) gene, a polyadenylation signal sequence derived from the pea ssRUBISCO E9 gene and a polyadenylation signal sequence derived from the α-tubulin gene.

The "effectively linking" in the present invention indicates binding of a nucleic acid sequence, wherein the binding enables a sequence to provide a function required for the linked sequence. The "effectively linking" in the present invention can link a promoter to a sequence of interest, so that the transcription of the sequence of interest is controlled and regulated by the promoter. When a sequence of interest encodes a protein and the expression of the protein is desired, "effectively linking" means that: a promoter is linked to the sequence in such a manner that the resulting transcript is efficiently translated. If the linking of a promoter to a coding sequence is transcript fusion and expression of the encoded protein is intended to be achieved, such linking is created that the first translation initiation codon in the resulting transcript is the initiation codon in the coding sequence. Alternatively, if the linking of a promoter to a coding sequence is translation fusion and expression of the encoded protein is intended to be achieved, such a linking is created that the first translation initiation codon contained in the 5' untranslated sequence is linked to the promoter in such a manner that the relationship of the resulting translation product with the translation open reading frame encoding the desired protein is in-frame. Nucleic acid sequences that can be "effectively linked" include, but are not limited to: sequences providing gene expression functions (i.e., gene expression elements, such as promoters, 5' untranslated regions, introns, protein coding regions, 3' untranslated regions, polyadenylation sites and/or transcription terminators), sequences providing DNA transfer and/or integration functions (i.e., T-DNA boundary sequences, site-specific recombinase recognition sites and integrase recognition sites), sequences providing selective functions (i.e., antibiotic tolerance markers and biosynthesis genes), sequences providing marker scoring functions, sequences assisting in sequence manipulation in vitro or in vivo (i.e., polylinker sequences and site-specific recombination sequences) and sequences providing replication functions (i.e., bacterial origins of replication, autonomously replicating sequences and centromeric sequences).

The present invention may confer a new herbicide tolerance trait to a plant, and no adverse effects on phenotypes (including yields) are observed. The plant in the present invention can tolerate, e.g., 1× application level of at least one herbicide tested. The improvement of these levels of tolerance is within the scope of the present invention. For example, foreseeable optimization and further development can be performed on various techniques known in the art, to increase the expression of a given gene.

In the present invention, the herbicide resistant protein is of the MTHFR66 amino acid sequence shown as SEQ ID NO: 2 in the sequence listing. The herbicide resistant gene is of the MTHFR66 nucleotide sequence shown as SEQ ID NO: 1 in the sequence listing. The herbicide resistant gene can contain, apart from a coding region of protein encoded by MTHFR66 nucleotide sequence, other elements for use in plants, for example a coding region encoding a transit peptide, a coding region encoding a selective marker protein or a protein imparting insect tolerance.

The herbicide resistant MTHFR66 protein in the present invention is tolerant to a dicamba herbicide. The plant in the present invention contains an exogenous DNA in its genome, wherein the exogenous DNA comprises the MTHFR66 nucleotide sequence, and the plant is protected from the threat of a herbicide by expressing an effective amount of the protein. The effective amount refers to a dose causing no or minor damage. At the same time, the plant should be morphologically normal and can be cultivated under conventional methods for product consumption and/or production.

The present invention provides a herbicide resistant protein, a coding gene thereof and use thereof, having the following advantages:
1. Having a strong herbicide tolerance. The MTHFR66 gene of the present invention can degrade a dicamba herbicide, and the optimized MTHFR66 gene uses preferred codons of maize and soybean, so that it is particularly suitable for expression in plants; the optimized MTHFR66 gene can impart transgenic plants the dicamba herbicide tolerance, and the optimized MTHFR66 gene located in the chloroplast for expression can enhance the tolerance of transgenic plants to a dicamba herbicide.
2. Broad application prospect. Herbicide resistant protein MTHFR66 of the present invention is methyltetrahydrofolate reductase, which is different from the known dicamba tolerant gene. Therefore, it is possible to expand the application scope of dicamba tolerance in plants.

The technical solution of the present invention is further described in details through drawings and examples below.

PARTICULAR EMBODIMENTS

Figure 1:
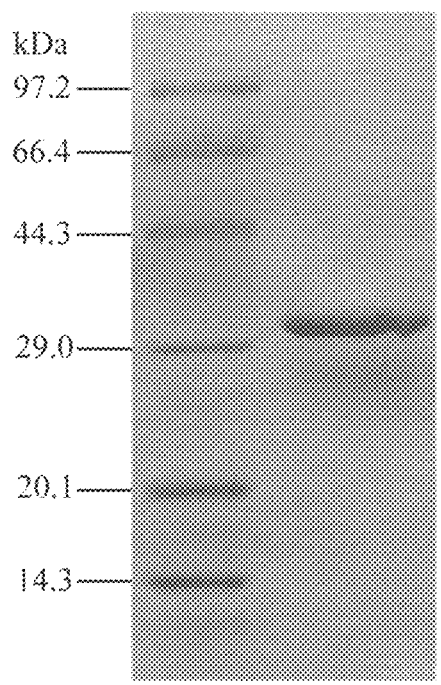
FIG. 1 is a SDS-PAGE electrophoretogram of the protein expressed by MTHFR66 gene in expression host bacterium BL21 (DE3) for a herbicide resistant protein, a coding gene thereof and use thereof in the present invention.

The technical solutions of the herbicide resistant protein, the coding gene thereof and use thereof in the present invention are further described through specific examples below.

Example 1

In Vitro Efficient Expression and Functional Identification of Methyltetrahydrofolate Reductase MTHFR66

1. Construction of a Bacterial Expression Vector and Acquisition of a Recombinant Microorganism (1) PCR amplification of MTHFR66 gene
A pair of primers were designed:

```
primer 1:
5-GGAATTCCATATGGGCTCGCCCGTTATGG-3
(the sequence underlined is NdeI restriction
site), shown as SEQ ID NO: 4 in the sequence
listing;

primer 2:
5-CCGCTCGAGGTGCTTTCGAGCGTAGTCAG-3
(the sequence underlined is XhoI restriction
site), shown as SEQ ID NO: 5 in the sequence
listing;
``` the MTHFR66 gene was amplified using the following PCR amplification system:

| | |
|---|---|
| Taq DNA polymerase (5 U/μL) | 0.5 μL |
| 5 × PrimeSTARBuffer (Mg$^{2+}$Plus) | 25 μL |
| dNTP mixture (each 2.5 mM) | 5 μL |
| Template DNA | 10 ng |
| Primer 1 (25 μM) | 1 μL |
| Primer 2 (25 μM) | 1 μL |
| Total volume | 50 μL |

The template DNA (i.e. the natural MTHFR66 nucleotide sequence) is shown as SEQ ID NO: 3 in the sequence listing. PCR reaction conditions: denaturation at 98° C. for 1 min; then entering the following cycle: denaturation at 98° C. for 15 s, annealing at 55° C. for 15 s, extension at 72° C. for 1 min, totally including 29 cycles; finally extension at 72° C. for 10 min, and cooling to room temperature.

(2) Construction of a bacterial expression vector and acquisition of a recombinant microorganism The above PCR amplification product and a bacterial expression vector pET-29a (+) were digested respectively with restriction enzymes NdeI and XhoI, the excised MTHFR66 nucleotide sequence fragment was enzymatically linked with the bacterial expression vector pET-29a (+) after enzyme digestion, and the expression host strain BL21 (DE3) was transformed with the enzymatically linked products to obtain the recombinant microorganism BL21 (MTHFR66).

2. Expression and Purification of MTHFR66 Protein in *E. coli*

The recombinant microorganism BL21 (MTHFR66) was cultured in 100 mL of LB medium (10 g/L of tryptone, 5 g/L of yeast extract, 10 g/L of NaCl and 100 mg/L of kanamycin, adjusted to pH 7.5 with NaOH) to a concentration of OD600 nm=0.6-0.8, and induced with isopropyl thiogalactoside (IPTG) at a concentration of 0.4 mM at a temperature of 16° C. for 20 hours. Bacterial cells were collected by centrifugation and resuspended in 20 ml of Tris-HCl buffer (100 mM, pH 8.0), followed by performing ultrasonication (X0-900D ultrasonic processor ultrasonic processor, 30% intensity) for 10 min, then centrifuging, collecting the supernatant, purifying the MTHFR66 protein with nickel ion affinity chromatography column, and detecting the purification result using SDS-PAGE protein electrophoresis with the stripe size being consistent with theoretically predicted stripe size (31.79 kDa) (as shown in FIG. 1).

3. Determination of Enzymatic Activity of MTHFR66 Protein

Enzymatic reaction system (300 μL): containing 1 mM substrate (dicamba), 0.2 mg of MTHFR66, 1 mM tetrahydrofolate (THF) and a buffer system of Tris-HCl at a concentration of 100 mM (pH 8.0), which were reacted in a water bath at a temperature of 30° C. for 1 hour, then kept in boiling water for 1 min, after which the reaction was terminated. The reaction solution was lyophilized, and then dissolved by adding 300 μl of methanol. The amount of the generated intermediate metabolite of dicamba, 3,6-dichlorosalicylic acid (DCSA), was detected using high performance liquid chromatography (HPLC). An enzymatic activity unit is defined as: the amount of enzyme required for degradation of dicamba to generate 1 nmol of product DCSA at pH 8.0, at a temperature of 30° C. within 1 min, and is expressed as U.

Figure 2:
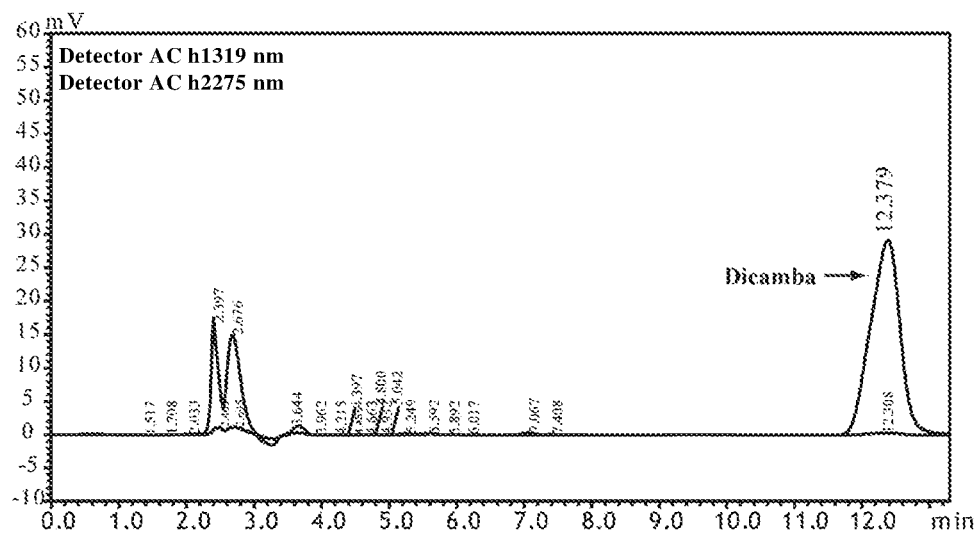
FIG. 2 is a HPLC chromatogram of dicamba degraded by inducibly expressed MTHFR66 protein for the herbicide resistant protein, the coding gene thereof and use thereof in the present invention.
Figure 2:
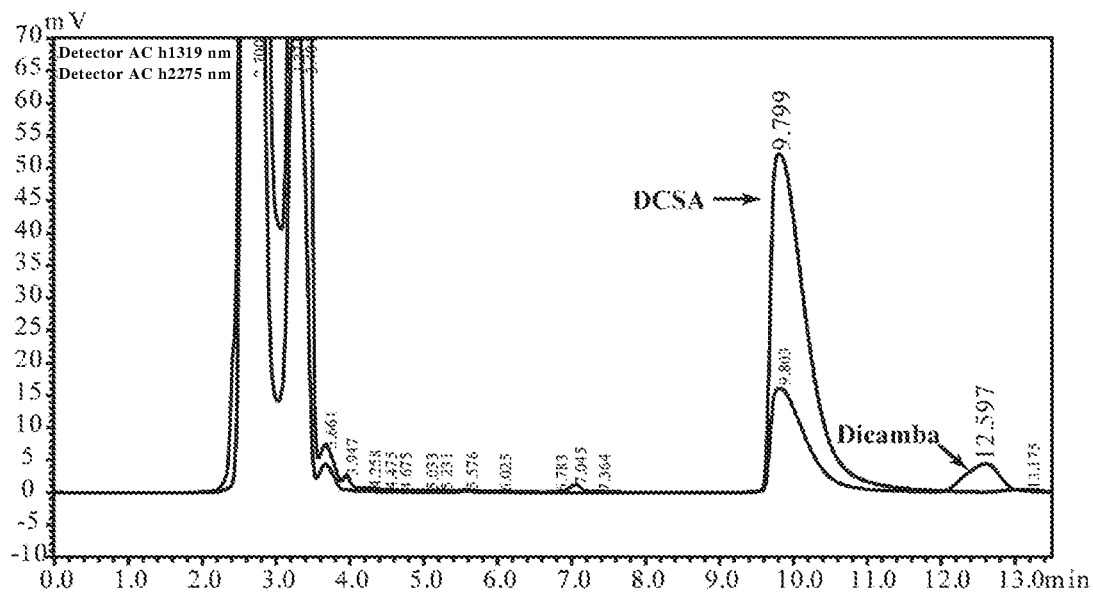

The above experimental results showed that: purified MTHFR66 protein can generate 0.15 mM DCSA within 1 hour, and the specific enzymatic activity of MTHFR66 protein was 3.75 U/mg (as shown in FIG. 2).

4. Determination of the Dicamba Demethylation Function of MTHFR66 Protein in the Presence of Trace Tetrahydrofolate Enzymatic reaction system (300 μL): containing 1 mM substrate (dicamba), 0.2 mg of MTHFR66, respectively containing 0.01 mM, 0.02 mM, 0.05 mM and 1 mM tetrahydrofolate (THF), and a buffer system of Tris-HCl at a concentration of 100 mM (pH 8.0), which were reacted in a water bath at a temperature of 30° C. for 1 hour, then kept in boiling water for 1 min followed by terminating the reaction. The reaction solution was lyophilized, and then dissolved by adding 300 μl of methanol. The amount of the generated intermediate metabolite of dicamba, DCSA, was detected using high performance liquid chromatography (HPLC).

Figure 3:
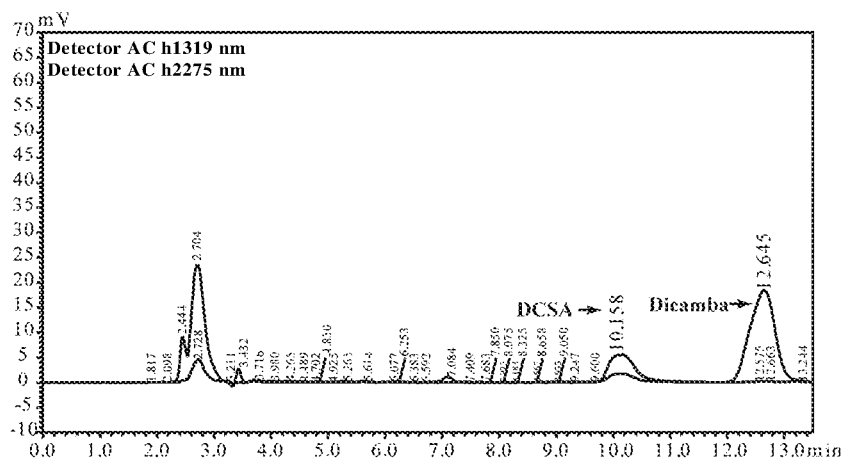
FIG. 3 is a HPLC chromatogram of dicamba degraded by inducibly expressed MTHFR66 protein in the presence of different concentrations of tetrahydrofolate for the herbicide resistant protein, the coding gene thereof and use thereof in the present invention.
Figure 3:
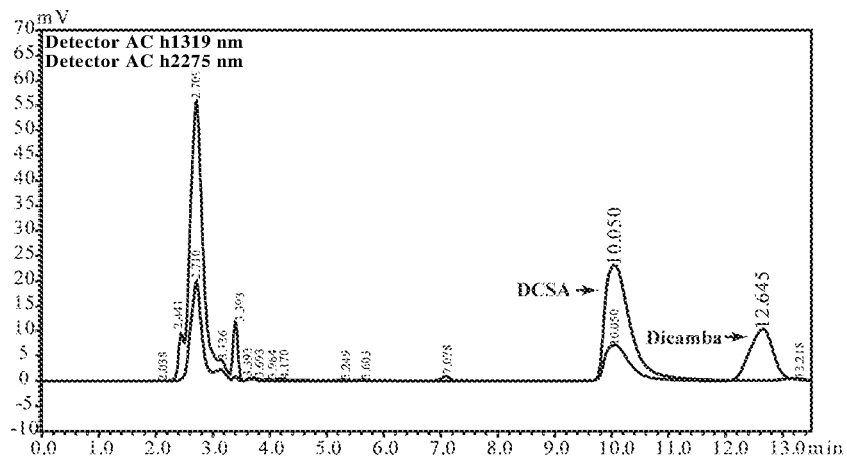
Figure 3:
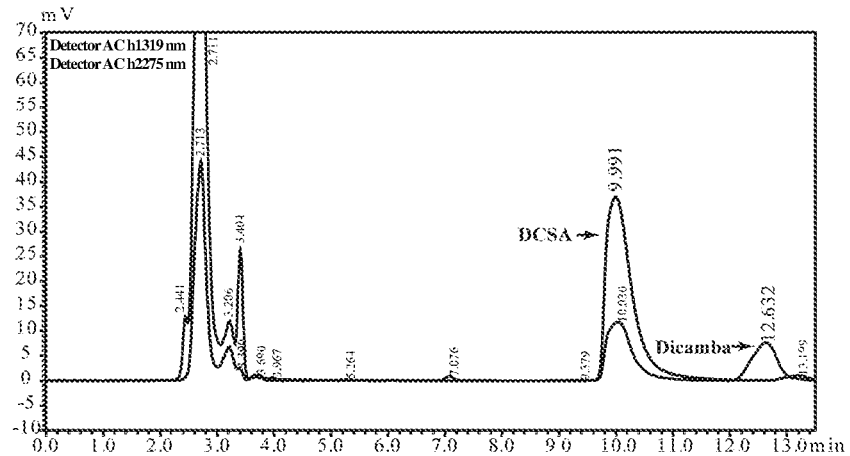
Figure 3:
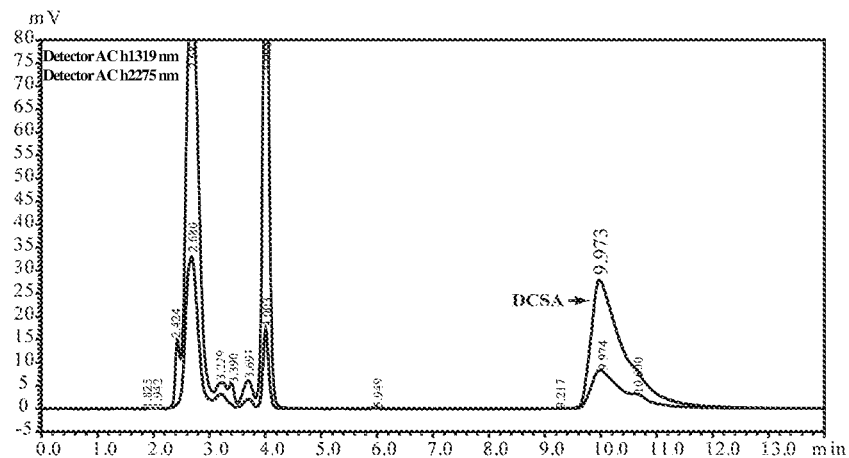
Figure 3:
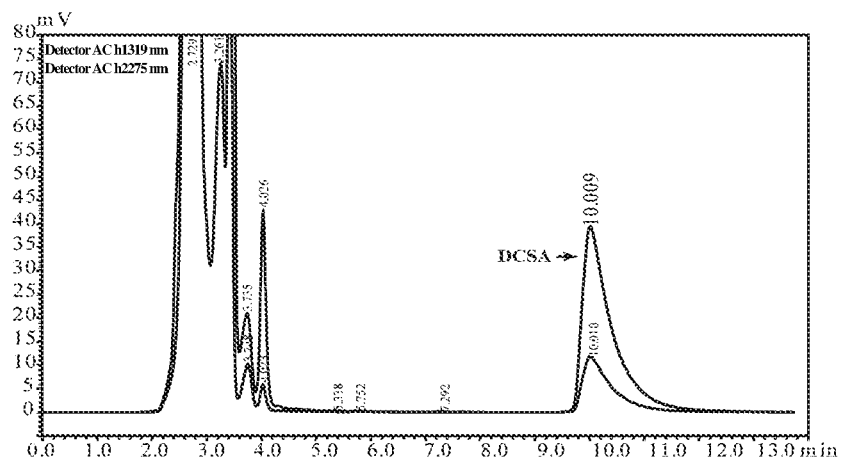

The above experimental results showed that: purified MTHFR66 protein can demethylate dicamba to generate DCSA in the presence of 0.01 mM tetrahydrofolate, and can fully demethylate 1 mM dicamba to generate DCSA in the presence of 0.5 mM of tetrahydrofolate (as shown in FIG. 3).

Example 2

Hydrolase Functional Identification and Product Identification of Methyltetrahydrofolate Reductase MTHFR66

1. Hydrolase Functional Determination of MTHFR66 Protein

Enzymatic reaction system (300 μL): containing 0.2 mg of MTHFR66, 1 mM 5-methyl-tetrahydrofolate (5-$CH_3$—$H_4F$) and a buffer system of Tris-HCl at a concentration of 100 mM (pH 8.0), which were reacted in a water bath at a temperature of 30° C. for 1 hour, then kept in boiling water for 1 min, after which the reaction was terminated. The reaction solution was lyophilized, dissolved by adding 300 μl of 0.1 mol/L $KH_2PO_4$ (pH 6.8, 1% ascorbic acid and 0.1% β-mercaptoethanol), filtered using a filter membrane (with a pore size of 0.22 μm), and detected using high performance liquid chromatography. Liquid chromatography conditions were: mobile phase: 0.05 mol/l $KH_2PO_4$ (pH 3.0):acetonitrile (90:10, V/V), Zorbax C218 ODS Spherex reversed phase column (5 μm, 4.6 mm×250 mm, Agilent, USA), column temperature of 23° C., UV-detector, with a detection wavelength of 298 nm, a sample injection volume of 20 μl, and a flow rate of 1.0 mL/min. Quantification was performed by peak area according to the external standard method.

Figure 4:
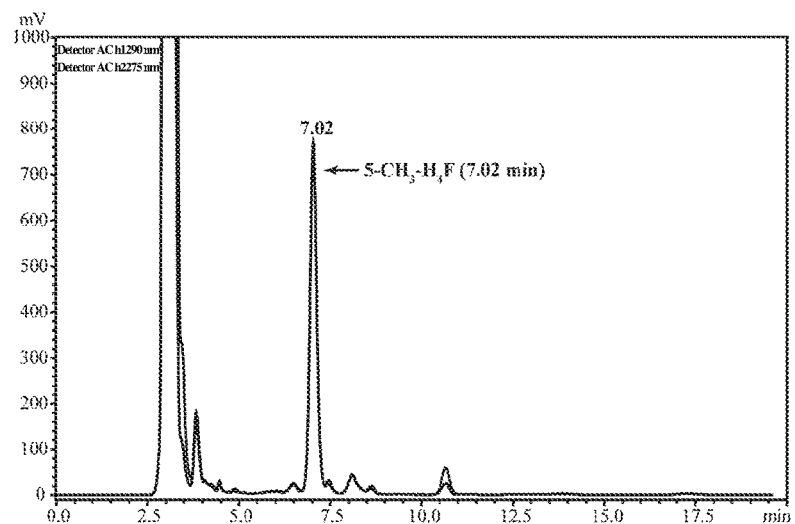
FIG. 4 is a HPLC chromatogram of 5-methyltetrahydrofolate metabolized by inducibly expressed MTHFR66 protein for the herbicide resistant protein, the coding gene thereof and use thereof in the present invention.
Figure 4:
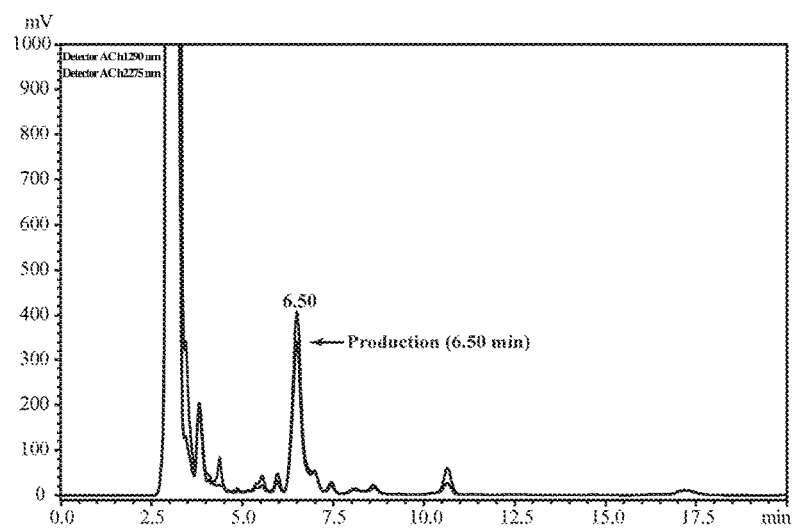

The above HPLC results showed that: purified MTHFR66 protein can transform 5-methyl-tetrahydrofolate to other substances in the absence of the electron acceptor $NAD^+$ (as shown in FIG. 4).

2. Product Identification

Metabolites were identified through HPLC-MS (high performance liquid chromatography-mass spectrum) under the conditions as follows: mobile phase: 0.05 mol/l $KH_2PO_4$ (pH 3.0):acetonitrile (90:10, V/V), Zorbax XDB-C18, 5 cm×0.46 cm, 1.8 mm reversed phase column (5 μm, 4.6 mm×250 mm, Agilent, USA), and a flow rate of 0.25 mL/min. MS analysis uses ESI mode and a detector of Agilent G6410B Triple Quad Mass Spectrometer.

Figure 5:
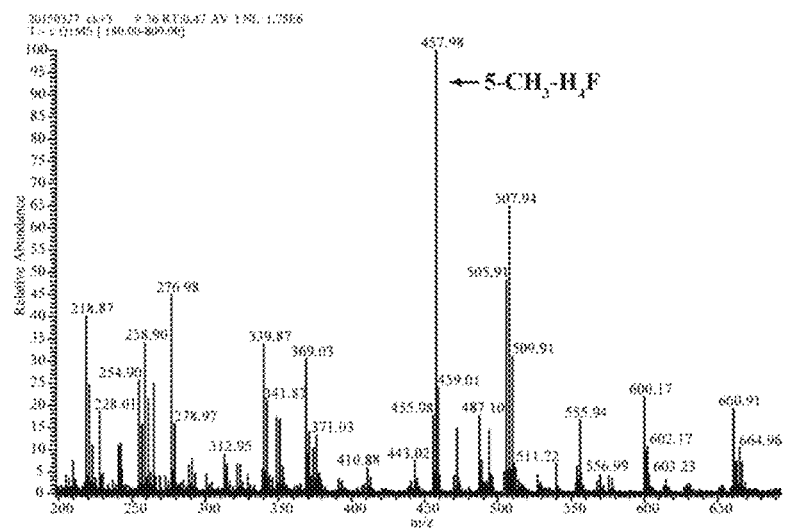
FIG. 5 is a first-stage mass spectrogram for identifying intermediate products of 5-methyltetrahydrofolate metabolized by inducibly expressed MTHFR66 protein for the herbicide resistant protein, the coding gene thereof and use thereof in the present invention.
Figure 5:
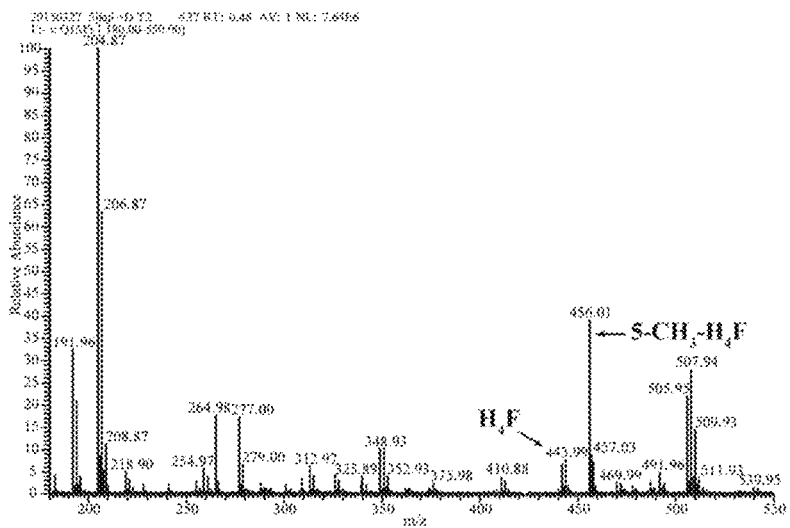

The results suggested that purified MTHFR66 protein can hydrolyze 5-methyl-tetrahydrofolate to tetrahydrofolate in the absence of the electron acceptor $NAD^+$ (as shown in FIG. 5).

Example 3

Gene Sequence Optimization and Synthesis

1. Acquisition of Optimized Plant Sequence

The amino acid sequences (289 amino acids, shown as SEQ ID NO: 2 in the sequence listing) of the methyltetrahydrofolate reductase MTHFR66 were kept unchanged, and codon optimization and modification of the MTHFR66 nucleotide sequence (870 nucleotides) encoding the amino acid sequence corresponding to the methyltetrahydrofolate reductase MTHFR66 was performed.

Codon optimization and modification strategies mainly include: depending on preferred codons of monocotyledonous maize plants and dicotyledonous soybean plants, unstable sequence modification, G+C content improvement, etc. Natural genes contain a low content of G+C, but a high content of A+T. On the one hand, if natural gene sequences are directly introduced into plant genomes, they may be mistaken for plant gene regulatory sequences, besides, A+T-rich regions will arise in these natural genes, similar to the TATA box in the gene promoter, and will lead to abnormal gene transcription; on the other hand, the polyadenylation signal sequence (AAUAAA) in the transcribed mRNA and small RNA complementary sequence associated with the mRNA splicing will lead to unstability of RNA. Therefore, the modified gene sequence not only has a high content of G+C, but also changes the unstable structure arising in DNA and transcribed mRNA, so as to ensure normal protein translation; on the other hand, preferred codons of maize and soybean are used to modify natural gene sequences, and eliminate the modification of restriction sites and some sequences.

Based on the above optimization strategies, an optimized MTHFR66 nucleotide sequence are obtained, the optimized MTHFR66 nucleotide sequence totally contains 870 nucleotides, and encodes 289 amino acids, and the nucleotide sequence is shown as SEQ ID NO: 1 in the sequence listing.

2. Synthesis of an Optimized MTHFR66 Nucleotide Sequence

The optimized MTHFR66 nucleotide sequence was synthesized by GenScript (Nanjing) Co., Ltd; and the synthetic optimized MTHFR66 nucleotide sequence (SEQ ID NO: 1) is further connected with a SadI restriction site at the 5' terminus, and the optimized MTHFR66 nucleotide sequence (SEQ ID NO: 1) is further connected with a KasI restriction site at the 3' terminus.

Example 4

Figure 6:
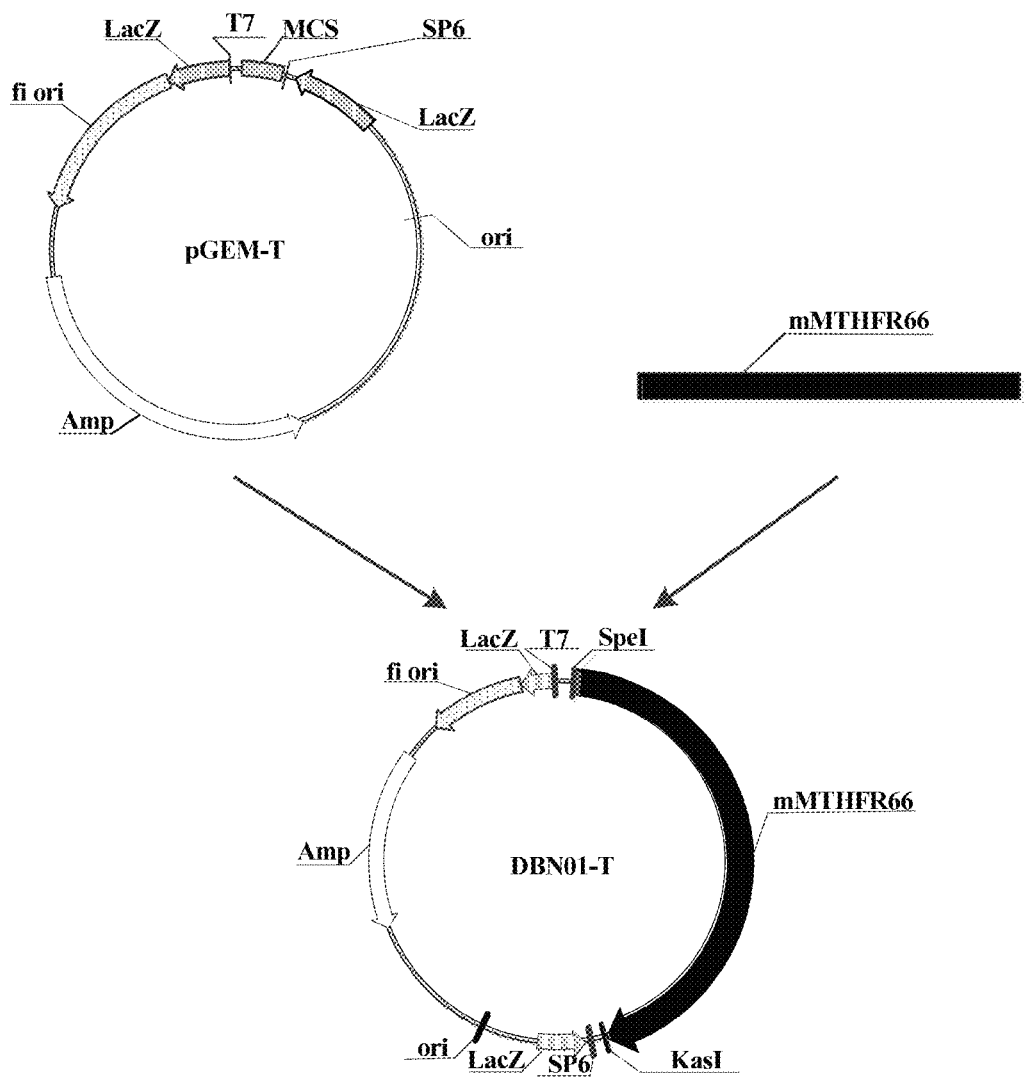
FIG. 6 is a construction flow chart of a recombinant cloning vector DBN01-T containing an optimized MTHFR66 nucleotide sequence for the herbicide resistant protein, the coding gene thereof and use thereof of the present invention.

Construction of *Arabidopsis thaliana* Recombinant Expression Vectors and Transformation of *Agrobacterium* with the Recombinant Expression Vectors 1. Construction of an *Arabidopsis thaliana* Recombinant Cloning Vector Containing an Optimized MTHFR66 Nucleotide Sequence The synthetic optimized MTHFR66 nucleotide sequence was ligated into cloning vector pGEM-T (Promega, Madison, USA, CAT: A3600), and the operational procedure was carried out according to Promega's pGEM-T vector product instructions, obtaining a recombinant cloning vector DBN01-T, the construction process of which was shown as FIG. 6 (wherein, Amp means the ampicillin resistance gene; f1 means the origin of replication of phage f1; LacZ is LacZ initiation codon; SP6 is SP6 RNA polymerase promoter; T7 is T7 RNA polymerase promoter; MTHFR66 is the optimized MTHFR66 nucleotide sequence (SEQ ID NO: 1); and MCS is a multiple cloning site).

Then, *Escherichia coli* T1 competent cells (Transgen, Beijing, China, CAT: CD501) were transformed with the recombinant cloning vector DBN01-T using the heat shock method with the following heat shock conditions: water bathing 50 μL *Escherichia coli* T1 competent cells and 10 μL plasmid DNA (recombinant cloning vector DBN01-T) at 42° C. for 30 seconds; shake culturing at 37° C. for 1 hour (using a shaker at a rotation speed of 100 rpm for shaking); and growing on an LB plate (10 g/L of tryptone, 5 g/L of yeast extract, 10 g/L of NaCl, and 15 g/L of agar, adjusting the pH to 7.5 with NaOH) of ampicillin (100 mg/L) having its surface coated with IPTG (isopropylthio-β-D-galactoside) and X-gal (5-bromo-4-chloro-3-indole-β-D-galactoside) overnight. White colonies were picked out and cultured in an LB liquid culture medium (10 g/L of tryptone, 5 g/L of yeast extract, 10 g/L of NaCl, and 100 mg/L of ampicillin, adjusting the pH to 7.5 with NaOH) at a temperature of 37° C. overnight. The plasmids in the cells were extracted through an alkaline method: centrifuging the bacteria solution at a rotation speed of 12000 rpm for 1 min, removing the supernatant, and suspending the precipitated thalli with 100 μL ice pre-cooled solution I (25 mM Tris-HCl, 10 mM EDTA (ethylenediaminetetraacetic acid), and 50 mM glucose, pH 8.0); adding 200 μL newly formulated solution II (0.2M NaOH, 1% SDS (sodium dodecyl sulfate)), inverting the tube 4 times, mixing and placing on ice for 3-5 min; adding 150 μL ice-cold solution III (3 M potassium acetate, 5 M acetic acid), mixing uniformly immediately and placing on ice for 5-10 min; centrifuging under the conditions of a temperature of 4° C. and a rotation speed of 12000 rpm for 5 min, adding 2 volumes of anhydrous ethanol to the supernatant and placing at room temperature for 5 min after mixing uniformly; centrifuging under the conditions of a temperature of 4° C. and a rotation speed of 12000 rpm for 5 min, discarding the supernatant, and air drying the precipitate after washing with ethanol with a concentration of 70% (V/V); adding 30 μL TE (10 mM Tris-HCl, and 1 mM EDTA, pH 8.0) containing RNase (20 μg/mL) to dissolve the precipitate; water bathing at a temperature of 37° C. for 30 min to digest RNA; and storing at a temperature of −20° C. for use.

After identifying the extracted plasmid by SacI and KasI digestion, positive clones were verified by sequencing. The results showed that the optimized MTHFR66 nucleotide sequence inserted in the recombinant cloning vector DBN01-T was the nucleotide sequence shown as SEQ ID NO: 1 in the sequence listing, that is, the optimized MTHFR66 nucleotide sequence was inserted correctly.

Figure 7:
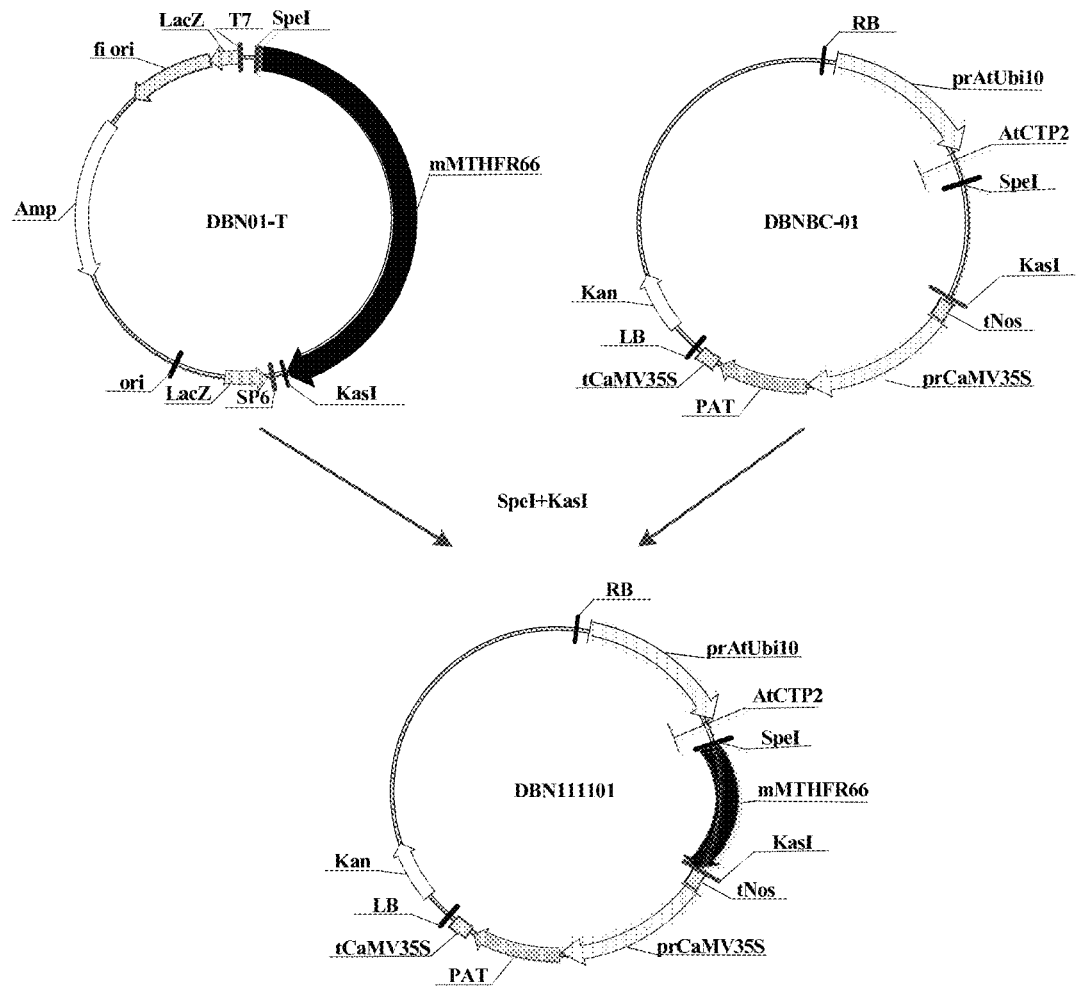
FIG. 7 is a construction flow chart of a recombinant expression vector DBN111101 containing an optimized MTHFR66 nucleotide sequence for the herbicide resistant protein, the coding gene thereof and use thereof in the present invention.

2. Construction of *Arabidopsis thaliana* Recombinant Expression Vector DBN111101 Containing an Optimized MTHFR66 Nucleotide Sequence The recombinant cloning vector DBN01-T and an expression vector DBNBC-01 (vector backbone: pCAMBIA2301 (which can be provided by the CAMBIA institution)) were digested with restriction enzymes SacI and KasI, respectively; the excised optimized MTHFR66 nucleotide sequence fragment was inserted between the SacI and KasI sites in the expression vector DBNBC-01; and it is well known to a person skilled in the art to construct a vector using conventional enzyme digestion methods, a recombinant expression vector DBN111101 was constructed, and the construction process of which was shown as FIG. 7 (Kan: kanamycin gene; RB: the right boundary; prAt Ubi10: the *Arabidopsis thaliana* Ubiquitin 10 gene promoter (SEQ ID NO: 6); At CTP2: the *Arabidopsis thaliana* chloroplast transit peptide (SEQ ID NO: 7); mMTHFR66: the optimized MTHFR66 nucleotide sequence (SEQ ID NO: 1); tNos: the terminator of nopaline synthase gene (SEQ ID NO:8); prCaMV35S: the cauliflower mosaic virus 35S promoter (SEQ ID NO: 9); PAT: the glufosinate acetyltransferase gene (SEQ ID NO: 10); tCaMV35S: the cauliflower mosaic virus 35S terminator (SEQ ID NO: 11); LB: the left boundary).

*Escherichia coli* T1 competent cells were transformed with the recombinant expression vector DBN111101 by a heat shock method with the following heat shock conditions: water bathing 50 μL *Escherichia coli* T1 competent cells and 10 μL plasmid DNA (recombinant expression vector DBN111101) at 42° C. for 30 seconds; shake culturing at 37° C. for 1 hour (using a shaker at a rotation speed of 100 rpm for shaking); then culturing under the condition of a temperature of 37° C. on an LB solid plate containing 50 mg/L of kanamycin (10 g/L of tryptone, 5 g/L of yeast extract, 10 g/L of NaCl, and 15 g/L of agar, adjusted to a pH of 7.5 with NaOH) for 12 hours, picking white colonies, and culturing under the condition of a temperature of 37° C. overnight in an LB liquid culture medium (10 g/L of tryptone, 5 g/L of yeast extract, 10 g/L of NaCl, and 50 mg/L of kanamycin, adjusted to a pH of 7.5 with NaOH). The plasmids in the cells were extracted through an alkaline method. The extracted plasmid was identified after digesting with restriction enzymes SacI and KasI, and positive clones were identified by sequencing. The results showed that the nucleotide sequence between the SacI and KasI sites in the recombinant expression vector DBN111101 was the nucleotide sequence shown as SEQ ID NO: 1 in the sequence listing, i.e., the optimized MTHFR66 nucleotide sequence.

3. Construction of *Arabidopsis thaliana* Recombinant Expression Vector DBN111101N Containing a Natural MTHFR66 Nucleotide Sequence The recombinant cloning vector DBN01R1-T containing a natural MTHFR66 nucleotide sequence was constructed using the natural MTHFR66 nucleotide sequence (SEQ ID NO: 3) according to the method for constructing the recombinant cloning vector DBN01-T containing the optimized MTHFR66 nucleotide sequence as described in point 1 of this example. Positive clones were verified by sequencing. The results showed that the natural MTHFR66 nucleotide sequence inserted in the recombinant cloning vector DBN01R-T was the nucleotide sequence shown as SEQ ID NO: 3 in the sequence listing, that is, the natural MTHFR66 nucleotide sequence was inserted correctly.

Figure 8:
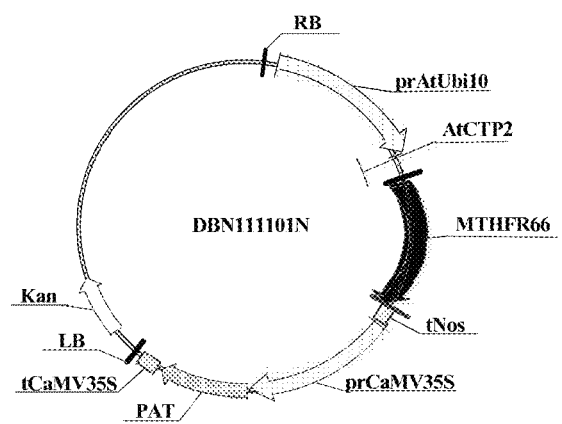
FIG. 8 is a structural diagram of a recombinant expression vector DBN111101 containing a natural MTHFR66 nucleotide sequence for the herbicide resistant protein, the coding gene thereof and use thereof in the present invention.

The recombinant expression vector DBN111101N containing natural MTHFR66 nucleotide sequence was constructed using the natural MTHFR66 nucleotide sequence according to the method for constructing the recombinant expression vector DBN111101 containing the optimized MTHFR66 nucleotide sequence as described in point 2 of this example, and has a structure as shown in FIG. 8 (vector backbone: pCAMBIA2301 (which can be provided by the CAMBIA institution); Kan: kanamycin gene; RB: the right boundary; prAt Ubi10: the *Arabidopsis thaliana* Ubiquitin 10 gene promoter (SEQ ID NO: 6); At CTP2: the *Arabidopsis thaliana* chloroplast transit peptide (SEQ ID NO: 7); MTHFR66: the natural MTHFR66 nucleotide sequence (SEQ ID NO: 3); tNos: the terminator of nopaline synthase gene (SEQ ID NO:8); prCaMV35S: the cauliflower mosaic virus 35S promoter (SEQ ID NO: 9); PAT: the glufosinate acetyltransferase gene (SEQ ID NO: 10); tCaMV35S: the cauliflower mosaic virus 35S terminator (SEQ ID NO: 11); LB: the left boundary). Positive clones were verified by sequencing. The results showed that the natural MTHFR66 nucleotide sequence inserted in the recombinant expression vector DBN111101N was the nucleotide sequence shown as SEQ ID NO: 3 in the sequence listing, that is, the natural MTHFR66 nucleotide sequence was inserted correctly.

4. Transformation of *Agrobacterium* with the *Arabidopsis thaliana* Recombinant Expression Vectors The *Agrobacterium* GV3101 was transformed with the recombinant expression vectors DBN111101 and DBN111101N which had been correctly constructed using the liquid nitrogen method with the following transformation conditions: placing 100 μL of *Agrobacterium* GV3101, and 3 μL of plasmid DNA (recombinant expression vector) in liquid nitrogen for 10 minutes, warm water bathing at 37° C. for 10 minutes; inoculating the transformed *Agrobacterium* GV3101 into an LB tube, culturing under the conditions of a temperature of 28° C. and a rotation speed of 200 rpm for 2 hours, spreading on an LB plate containing 50 mg/L of rifampicin and 50 mg/L of kanamycin until positive single clones were grown, picking out single clones for culturing and extracting the plasmids thereof, and performing enzyme digestion verification using restriction enzymes digesting DBN111101 and DBN111101N. The results showed that the structures of the recombinant expression vectors DBN111101 and DBN111101N were completely correct.

Example 5

Acquisition of the Transgenic *Arabidopsis thaliana* Plants

Seeds of wild-type *Arabidopsis thaliana* were suspended in a 0.1% agarose solution. The suspended seeds were stored at 4° C. for 2 days to complete the need for dormancy, in order to ensure synchronous seed germination. Vermiculite was mixed with horse manure soil, the mixture was sub-irrigated with water to wet, and the soil mixture was allowed to drain the water away for 24 hours. The pretreated seeds were sowed in the soil mixture and covered with a moisturizing cover for 7 days. The seeds were germinated and the plants were cultivated in a greenhouse under long day conditions (16 hour light/8 hour dark) of a constant temperature (22° C.) and a constant humidity (40-50%) with a light intensity of 120-150 μmol/(m$^2$·sec). The plants were initially irrigated with the Hoagland's nutrient solution, followed by deionized water, keeping the soil moist but not wet through.

*Arabidopsis thaliana* was transformed using the flower soaking method. One or more 15-30 mL of precultures of YEP culture solution (containing kanamycin (100 mg/L) and rifampicin (10 mg/L)) were inoculated with the picked Agrobacterium colonies. The cultures were incubated at 28° C. and 220 rpm with shaking at a constant speed overnight. Each preculture was used to inoculate two 500 ml of cultures of YEP culture solution (containing kanamycin (100 mg/L) and rifampicin (10 mg/L)), and the cultures were incubated at 28° C. with continuous shaking overnight. Cells were precipitated by centrifuging at about 8700×g at room temperature for 10 minutes, and the resulting supernatant was discarded. The cell precipitate was gently re-suspended in 500 mL osmotic medium which contained 1/2×MS salt/B5 vitamin, 10% (w/v) sucrose, 0.044 μM benzylaminopurine (10 μL/L (1 mg/mL, a stock solution in DMSO)) and 300 μL/L of Silvet L-77. About 1-month-old plants were soaked in a culture medium for 15 seconds to ensure immersion of the latest inflorescence. Then, the plants were reclined laterally and covered (transparently or opaquely) for 24 hours, then washed with water, and placed vertically. The plants were cultivated with a photoperiod of 16 hour light/8 hour dark at 22° C. Seeds were harvested after soaking for about 4 weeks.

The newly harvested (the optimized MTHFR66 nucleotide sequence and the natural MTHFR66 nucleotide sequence) $T_1$ seeds were dried at room temperature for 7 days. The seeds were sowed in 26.5×51 cm germination disks, and 200 mg $T_1$ seeds (about 10000 seeds) were accepted per disk, wherein the seeds had been previously suspended in 40 mL of 0.1% agarose solution and stored at 4° C. for 2 days to complete the need for dormancy, in order to ensure synchronous seed germination.

Vermiculite was mixed with horse manure soil, the mixture was sub-irrigated with water to wet, and water was drained through gravity. The pretreated seeds (each 40 mL) were sowed evenly in the soil mixture using a pipette, and covered with a moisturizing cover for 4-5 days. The cover was removed 1 day before performing initial transformant selection by spraying glufosinate (used to select the co-transformed PAT gene) post emergence.

The $T_1$ plants were sprayed with a 0.2% solution of a Liberty herbicide (200 g ai/L of glufosinate) reusing a DeVilbiss compressed air nozzle at a spray volume of 10 mL/disc (703 L/ha) 7 days after planting (DAP) and 11 DAP (the cotyledon stage and 2-4 leaf stage, respectively), to provide an effective amount of glufosinate of 280 g ai/ha per application. Surviving plants (actively growing plants) were identified 4-7 days after the final spraying, and transplanted to 7 cm×7 cm square pots prepared with horse manure soil and vermiculite (3-5 plants/disc), respectively. The transplanted plants were covered with a moisturizing cover for 3-4 days, and placed in a 22° C. culture chamber or directly transferred into a greenhouse as previously. Then, the cover was removed, and at least 1 day before testing the ability of the MTHFR66 gene to provide dicamba herbicide tolerance, the plants were planted in a greenhouse (22±5° C., 50±30% RH, 14 hour light:10 hour dark, a minimum of 500 µE/m²s¹ natural+supplemental light).

Example 6

Detection of Herbicide Tolerance Effects of the Transgenic *Arabidopsis thaliana* Plants

*Arabidopsis thaliana* was first transformed with the MTHFR66 gene. $T_1$ transformants were initially selected from the background of untransformed seeds using a glufosinate selection scheme. The plants that were transformed with the recombinant expression vector DBN111101 were *Arabidopsis thaliana* plants (At mMTHFR66) into which an optimized MTHFR66 nucleotide sequence located in the chloroplast was introduced, and the plants that were transformed with the recombinant expression vector DBN111101N were *Arabidopsis thaliana* plants (At MTHFR66) into which a natural MTHFR66 nucleotide sequence located in the chloroplast was introduced. About 20000 $T_1$ seeds of At mMTHFR66 were screened, and 197 $T_1$ positive transformants (PAT gene) were identified with a transformation efficiency of about 1.0%; and about 20000 $T_1$ seeds of At MTHFR66 were screened, and 182 $T_1$ positive transformants (PAT gene) were identified with a transformation efficiency of about 0.91%. *Arabidopsis thaliana* $T_1$ plants (At-mMTHFR66) into which an optimized MTHFR66 nucleotide sequence was introduced, *Arabidopsis thaliana* $T_1$ plants (At-MTHFR66) into which a natural MTHFR66 nucleotide sequence was introduced and wild-type *Arabidopsis thaliana* plants (18 days after sowing) were tested for the herbicide tolerance effect to dicamba.

*Arabidopsis thaliana* $T_1$ plants into which an optimized MTHFR66 nucleotide sequence was introduced, *Arabidopsis thaliana* $T_1$ plants into which a natural MTHFR66 nucleotide sequence was introduced and wild-type *Arabidopsis thaliana* plants were sprayed with dicamba (560 g ae/ha, 1-fold field concentration) and a blank solvent (water) respectively. Plants were counted for the tolerance situations 7 days and 14 days after spraying: those having a consistent growth status with the blank solvent (water) group after 7 days were classified as highly resistant plants, those having curled rosette leaves after 7 days were classified as moderately resistant plants, those still not capable of bolting after 14 days were classified as lowly resistant plants, and those dead after 14 days were classified as non-resistant plants. Since each *Arabidopsis thaliana* $T_1$ plant was an independent transformation event, a significant difference in individual $T_1$ responses could be expected at a given dose. The results were shown as Table 1 and FIG. 9.

TABLE 1

Experimental results of the herbicide tolerance of transgenic *Arabidopsis thaliana* $T_1$ plants

| Treatment | *Arabidopsis thaliana* genotypes | Highly resistant | Moderately resistant | Lowly resistant | Non-resistant | Total |
|---|---|---|---|---|---|---|
| Blank solvent (water) | At-mMTHFR66 | 24 | 0 | 0 | 0 | 24 |
| | At-MTHFR66 | 23 | 0 | 0 | 0 | 23 |
| | wild-type | 20 | 0 | 0 | 0 | 20 |
| 560 g ae/ha dicamba (1 × dicamba) | At-mMTHFR66 | 0 | 18 | 0 | 5 | 23 |
| | At-MTHFR66 | 0 | 3 | 2 | 19 | 24 |
| | wild-type | 0 | 0 | 0 | 22 | 22 |

Figure 9:
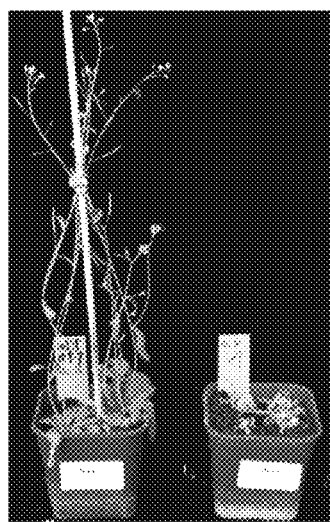
FIG. 9 is an effect diagram of the tolerance of a transgenic *Arabidopsis thaliana* $T_1$ plant to herbicides for the herbicide resistant protein, the coding gene thereof and use thereof in the present invention.
Figure 9:
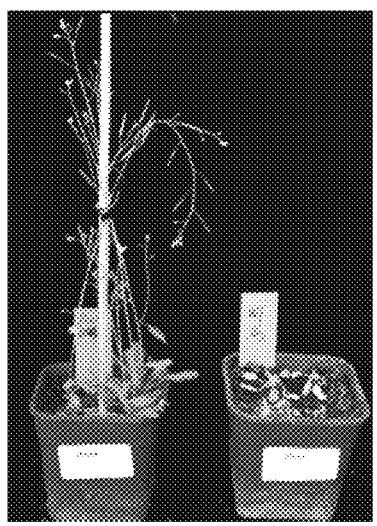
Figure 9:

For *Arabidopsis thaliana*, 560 g ae/ha dicamba is an effective dose distinguishing sensitive plants from plants having an average level of tolerance. The results of Table 1 and FIG. 9 showed that: the optimized MTHFR66 gene conferred dicamba herbicide tolerance to individual *Arabidopsis thaliana* plants (the reason why only some plants were tolerant was that the insertion site in the $T_1$ plants was random, so that the expression levels of the tolerance gene were different, showing a difference in tolerance level); compared to At-MTHFR66 $T_1$ plants, At-mMTHFR66 $T_1$ *Arabidopsis thaliana* progenies can generate higher dicamba herbicide tolerance, showing that the MTHFR66 gene can enhance the tolerance of *Arabidopsis thaliana* plants to a dicamba herbicide after the plant codon optimization; while the wild-type *Arabidopsis thaliana* does not have dicamba herbicide tolerance.

Example 7

Construction of Maize Recombinant Expression Vectors and Transformation of *Agrobacterium* with the Recombinant Expression Vectors 1. Construction of Maize Recombinant Expression Vector DBN-HT130066 Containing an Optimized MTHFR66 Nucleotide Sequence The recombinant cloning vector DBN01-T and an expression vector DBNBC-02 (vector backbone: pCAMBIA2301

Figure 10:
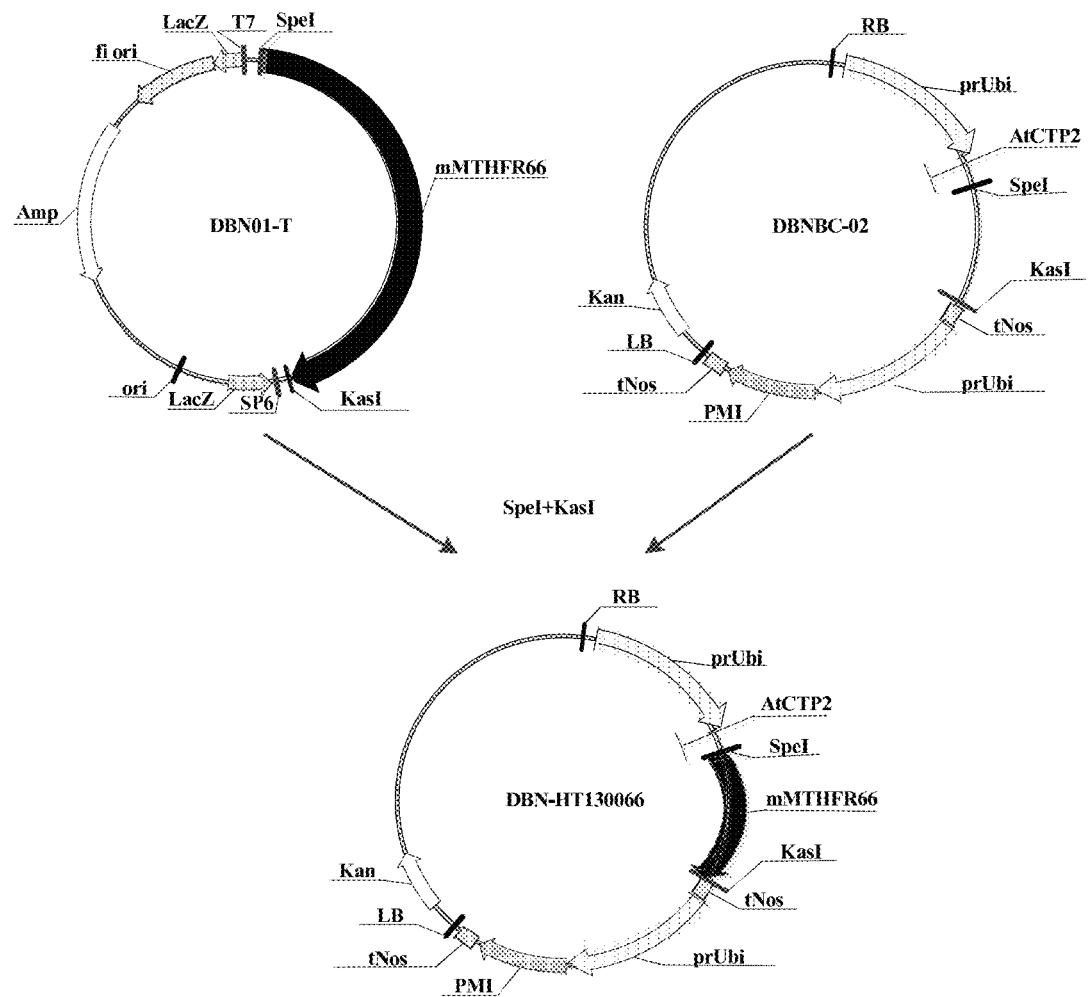
FIG. 10 is a construction flow chart of a recombinant expression vector DBN130066 containing an optimized MTHFR66 nucleotide sequence for the herbicide resistant protein, the coding gene thereof and use thereof in the present invention.

(which can be provided by the CAMBIA institution)) were digested with restriction enzymes SacI and KasI, respectively, and the excised optimized MTHFR66 nucleotide sequence fragment was inserted between the SacI and KasI sites in the expression vector DBNBC-02; and it is well known to a person skilled in the art to construct a vector using conventional enzyme digestion methods, a recombinant expression vector DBN-HT130066 was constructed, and the construction process of which was shown as FIG. 10 (Kan: kanamycin gene; RB: the right boundary; prUbi: the maize Ubiquitin 1 gene promoter (SEQ ID NO: 12); At CTP2: the *Arabidopsis thaliana* chloroplast transit peptide (SEQ ID NO: 7); mMTHFR66: the optimized MTHFR66 nucleotide sequence (SEQ ID NO: 1); tNos: the terminator of nopaline synthase gene (SEQ ID NO:8); PMI: the phosphomannose isomerase gene (SEQ ID NO: 13); LB: the left boundary).

*Escherichia coli* T1 competent cells were transformed with the recombinant expression vector DBN-HT130066 by a heat shock method with the following heat shock conditions: water bathing 50 μL *Escherichia coli* T1 competent cells and 10 μL plasmid DNA (recombinant expression vector DBN-HT130066) at 42° C. for 30 seconds; shake culturing at 37° C. for 1 hour (using a shaker at a rotation speed of 100 rpm for shaking); then culturing under the condition of a temperature of 37° C. on an LB solid plate containing 50 mg/L of kanamycin (10 g/L of tryptone, 5 g/L of yeast extract, 10 g/L of NaCl, and 15 g/L of agar, adjusted to a pH of 7.5 with NaOH) for 12 hours, picking white colonies, and culturing under the condition of a temperature of 37° C. overnight in an LB liquid culture medium (10 g/L of tryptone, 5 g/L of yeast extract, 10 g/L of NaCl, and 50 mg/L of kanamycin, adjusted to a pH of 7.5 with NaOH). The plasmids in the cells were extracted through an alkaline method. The extracted plasmid was identified after digesting with restriction enzymes SacI and KasI, and positive clones were identified by sequencing. The results showed that the nucleotide sequence between the SacI and KasI sites in the recombinant expression vector DBN-HT130066 was the nucleotide sequence shown as SEQ ID NO: 1 in the sequence listing, i.e., the optimized MTHFR66 nucleotide sequence.

Figure 11:
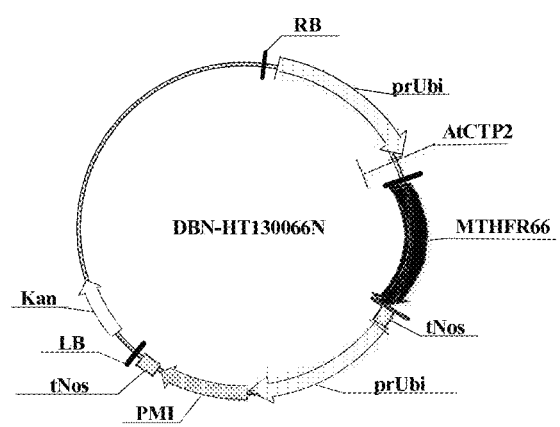
FIG. 11 is a structural diagram of a recombinant expression vector DBN-HT130066N containing a natural MTHFR66 nucleotide sequence for the herbicide resistant protein, the coding gene thereof and use thereof in the present invention.

2. Construction of Maize Recombinant Expression Vector DBN-HT130066N Containing a Natural MTHFR66 Nucleotide Sequence The recombinant expression vector DBN-HT130066N containing a natural MTHFR66 nucleotide sequence was constructed using the recombinant cloning vector DBN01R-T containing the natural MTHFR66 nucleotide sequence as described in point 3 of Example 4 of the present invention according to the method for constructing the recombinant expression vector DBN-HT120066 containing the optimized MTHFR66 nucleotide sequence as described in point 1 of this example, and has a structure as shown in FIG. 11 (vector backbone: pCAMBIA2301 (which can be provided by the CAMBIA institution); Kan: kanamycin gene; RB: the right boundary; prUbi: the maize Ubiquitin 1 gene promoter (SEQ ID NO: 12); At CTP2: the *Arabidopsis thaliana* chloroplast transit peptide (SEQ ID NO: 7); MTHFR66: the natural MTHFR66 nucleotide sequence (SEQ ID NO: 3); tNos: the terminator of nopaline synthase gene (SEQ ID NO:8); PMI: the phosphomannose isomerase gene (SEQ ID NO: 13); LB: the left boundary). Positive clones were verified by sequencing. The results showed that the natural MTHFR66 nucleotide sequence inserted in the recombinant expression vector DBN-HT130066N was the nucleotide sequence shown as SEQ ID NO: 3 in the sequence listing, that is, the natural MTHFR66 nucleotide sequence was inserted correctly.

3. Transformation of *Agrobacterium* with the Maize Recombinant Expression Vectors

*Agrobacterium* LBA4404 (Invitrgen, Chicago, USA, CAT: 18313-015) was transformed with the recombinant expression vectors DBN-HT130066 and DBN-HT130066N which have been constructed correctly using a liquid nitrogen method, with the following transformation conditions: placing 100 μL of *Agrobacterium* LBA4404, and 3 μL of plasmid DNA (recombinant expression vector) in liquid nitrogen for 10 minutes, warm water bathing at 37° C. for 10 minutes; inoculating the transformed *Agrobacterium* LBA4404 into an LB tube, culturing under the conditions of a temperature of 28° C. and a rotation speed of 200 rpm for 2 hours, spreading on an LB plate containing 50 mg/L of rifampicin and 50 mg/L of kanamycin until positive single clones were grown, picking out single clones for culturing and extracting the plasmids thereof, and performing enzyme digestion verification after enzyme digestion of DBN-HT130066 and DBN-HT130066N using restriction enzymes. The results showed that the structures of the recombinant expression vectors DBN-HT130066 and DBN-HT130066N were completely correct.

Example 8

Acquisition and Verification of Transgenic Maize Plants

According to the conventionally used *Agrobacterium* infection method, young embryos of a sterile culture of maize variety Zong31 (Z31) were co-cultured with the *Agrobacterium* in point 3 of Example 7 of the present invention, so as to introduce T-DNA (including the maize Ubiquitin1 gene promoter sequence, the optimized MTHFR66 nucleotide sequence, the natural MTHFR66 nucleotide sequence, the AcCTP2 chloroplast transit peptide sequence, the PMI gene and the Nos terminator sequence) in the recombinant expression vectors DBN-HT130066 and DBN-HT130066N constructed in points 1 and 2 of Example 7 of the present invention into the maize chromosome, thereby obtaining maize plants (Zm-mMTHFR66) into which the optimized MTHFR66 nucleotide sequence located in chloroplast was introduced, and maize plants (Zm-MTHFR66) into which the natural MTHFR66 nucleotide sequence was introduced; meanwhile, wild type maize plants were used as the control.

As regards the *Agrobacterium*-mediated maize transformation, briefly, immature young embryos were separated from maize, and contacted with an *Agrobacterium* suspension, wherein the *Agrobacterium* can transfer the optimized MTHFR66 nucleotide sequence and the natural MTHFR66 nucleotide sequence to at least one cell of one of young embryos (step 1: infection step). In this step, the young embryos were preferably immersed in an *Agrobacterium* suspension ($OD_{660}$=0.4-0.6, an infection culture medium (4.3 g/L of MS salt, MS vitamin, 300 mg/L of casein, 68.5 g/L of sucrose, 36 g/L of glucose, 40 mg/L of acetosyringone (AS), and 1 mg/L of 2,4-dichlorphenoxyacetic acid (2,4-D), pH 5.3)) to initiate the inoculation. The young embryos were co-cultured with *Agrobacterium* for a period of time (3 days) (step 2: co-culturing step). Preferably, the young embryos were cultured in a solid culture medium (4.3 g/L of MS salt, MS vitamin, 300 mg/L of casein, 20 g/L of sucrose, 10 g/L of glucose, 100 mg/L of acetosyringone (AS), 1 mg/L of 2,4-dichlorphenoxyacetic acid (2,4-D), and 8 g/L of agar, pH 5.8) after the infection step. After this co-culturing stage, there can be an optional "recovery" step. In the "recovery" step, there may be at least one antibiotic (cephalosporin) known to inhibit the growth of Agrobacterium in a recovery culture medium (4.3 g/L of MS salt, MS vitamin, 300 mg/L of casein, 30 g/L of sucrose, 1 mg/L of 2,4-dichlorphenoxyacetic acid (2,4-D), and 3 g/L of phytagel, pH 5.8), without the addition of a selective agent for a plant transformant (step 3: recovery step). Preferably, the young embryos were cultured in a solid culture medium with an antibiotic but without a selective agent, to eliminate Agrobacterium and provide a recovery stage for the infected cells. Subsequently, the inoculated young embryos were cultured in a culture medium containing a selective agent (mannose), and growing transformed calli were selected (step 4: selection step). Preferably, the young embryos were cultured in a screening solid culture medium (4.3 g/L of MS salt, MS vitamin, 300 mg/L of casein, 30 g/L of sucrose, 12.5g/L of mannose, 1 mg/L of 2,4-dichlorphenoxyacetic acid (2,4-D), and 3 g/L of phytagel, pH 5.8) with a selective agent, resulting in selective growth of transformed cells. Then, plants were regenerated from the calli (step 5: regeneration step). Preferably, the calli grown on a culture medium containing a selective agent were cultured in solid culture media (MS differentiation culture medium and MS rooting culture medium) to regenerate plants.

Resistant calli screened out were transferred onto the MS differentiation culture medium (4.3 g/L of MS salt, MS vitamin, 300 mg/L of casein, 30 g/L of sucrose, 2 mg/L of 6-benzyladenine, 5 g/L of mannose, and 3 g/L of phytagel, pH 5.8), and cultured at 25° C. for differentiation. The differentiated seedlings were transferred onto the MS rooting culture medium (2.15 g/L of MS salt, MS vitamin, 300 mg/L of casein, 30 g/L of sucrose, 1 mg/L of indole-3-acetic acid, and 3 g/L of phytagel, pH 5.8), cultured at 25° C. to a height of about 10 cm, and transferred to a glasshouse for culturing until fruiting. In the greenhouse, the plants were cultured at 28° C. for 16 hours, and then cultured at 20° C. for 8 hours every day.

2. Verification of the Transgenic Maize Plants Using TaqMan

Leaves of about 100 mg from maize plants into which the optimized MTHFR66 nucleotide sequence was introduced, and maize plants into which the natural MTHFR66 nucleotide sequence was introduced were respectively taken as samples, extracted for genomic DNAs thereof with a DNeasy Plant Maxi Kit of Qiagen, and detected for copy number of PMI gene by the Taqman probe fluorescence quantitative PCR method so as to determine the copy number in the transgenic maize plants. Meanwhile, wild type maize plants were used as the control, and detected and analyzed according to the above-mentioned method. Triple repeats were set for the experiments, and averaged.

The particular method for detecting the copy number of PMI gene was as follows:

Step 11. Leaves of 100 mg were respectively taken from each of maize plants into which the optimized MTHFR66 nucleotide sequence was introduced, maize plants into which the natural MTHFR66 nucleotide sequence was introduced, and wild type maize plants, respectively ground as a homogenate in a mortar with liquid nitrogen, and triple repeats were taken for each sample;

Step 12. Genomic DNAs of the above-mentioned samples were extracted using a DNeasy Plant Mini Kit of Qiagen, and the particular method can refer to the product manual thereof;

Step 13. The concentrations of the genomic DNAs of the above-mentioned samples were detected using NanoDrop 2000 (Thermo Scientific);

Step 14. The concentrations of the genomic DNAs of the above-mentioned samples were adjusted to a consistent concentration value which ranges from 80 to 100 ng/μL;

Step 15. The copy numbers of the samples were identified using the Taqman probe fluorescence quantitative PCR method, wherein samples for which the copy numbers had been identified and known were taken as standards, the samples of the wild type maize plants were taken as the control, and triple repeats were taken for each sample and averaged; the sequences of fluorescence quantitative PCR primers and a probe were as follows, respectively:

The following primers and probe were used to detect the PMI gene sequence:

```
primer 3:
CCGGGTGAATCAGCGTTT
shown as SEQ ID NO: 14 in the sequence listing;

primer 4:
GCCGTGGCCTTTGACAGT
shown as SEQ ID NO: 15 in the sequence listing;

probe 1:
TGCCGCCAACGAATCACCGG
shown as SEQ ID NO: 16 in the sequence listing;
```

PCR reaction system:

| | |
|---|---|
| JumpStart ™ Taq ReadyMix ™ (Sigma) | 10 μL |
| 50 × primer/probe mixture | 1 μL |
| genomic DNA | 3 μL |
| water (ddH₂O) | 6 μL |

The 50× primer/probe mixture comprises 45 μL of each primer at a concentration of 1 mM, 50 μL of the probe at a concentration of 100 μM, and 860 μL of 1×TE buffer, and was stored at 4° C. in an amber tube.

PCR reaction conditions:

| Step | Temperature | Time |
|---|---|---|
| 21 | 95° C. | 5 minutes |
| 22 | 95° C. | 30 seconds |
| 23 | 60° C. | 1 minute |
| 24 | back to step 22, repeated 40 times | |

Data were analyzed using software SDS2.3 (Applied Biosystems).

The experimental results showed that both the optimized MTHFR66 nucleotide sequence and the natural MTHFR66 nucleotide sequence were integrated into the chromosome of the detected maize plants, and both the maize plants into which the optimized MTHFR66 nucleotide sequence was introduced, and the maize plants into which the natural MTHFR66 nucleotide sequence was introduced resulted in transgenic maize plants containing single-copy MTHFR66 genes.

Example 9

Detection of Herbicide Resistance Effects of the Transgenic Maize Plants

The maize plants into which the optimized MTHFR66 nucleotide sequence was introduced, the maize plants into which the natural MTHFR66 nucleotide sequence was introduced and wild-type maize plants (at V5-V6 stage) were respectively tested for the herbicide resistance effect to dicamba.

The maize plants into which the optimized MTHFR66 nucleotide sequence was introduced, the maize plants into which the natural MTHFR66 nucleotide sequence was introduced and wild-type maize $T_1$ hybrid plants (at V5-V6 stage) were taken and sprayed with a dicamba herbicide (4480 g ae/ha, 8-fold field concentration) and a blank solvent (water) respectively. 21 days after spraying, the support root development situation was collected. A total of three strains (S1, S2 and S3) of Zm-mMTHFR66, a total of two strains (S4 and S5) of Zm-MTHFR66, and a total of 1 strain of wild type (CK) were taken; and 10-15 plants were selected from each strain and tested. The results were as shown in Table 2.

TABLE 2

Experimental results of the herbicide resistance of transgenic maize $T_1$ plants

| Treatment | Maize genotypes | Support root normally developed | Support root abnormally developed | Proportion of normally developed support root |
|---|---|---|---|---|
| Blank solvent (water) | S1 | 15 | 0 | 100.00% |
| | S2 | 16 | 0 | 100.00% |
| | S3 | 13 | 0 | 100.00% |
| | S4 | 11 | 0 | 100.00% |
| | S5 | 12 | 0 | 100.00% |
| | CK | 18 | 0 | 100.00% |
| 4480 g ae/ha dicamba (8 × dicamba) | S1 | 12 | 1 | 92.31% |
| | S2 | 10 | 1 | 90.91% |
| | S3 | 10 | 2 | 83.33% |
| | S4 | 2 | 10 | 16.67% |
| | S5 | 4 | 9 | 30.77% |
| | CK | 0 | 16 | 0% |

The results in Table 2 showed that The optimized MTHFR66 gene confers high-level dicamba herbicide tolerance to transgenic maize plants (monocotyledonous plant itself has certain resistance to the dicamba herbicide, thereby showing high-level resistance); compared to Zm-MTHFR66, Zm-mMTHFR66 can generate higher dicamba herbicide tolerance, showing that the MTHFR66 gene can enhance the dicamba herbicide tolerance of maize plants after the plant codon optimization; while the wild-type maize plants do not have dicamba herbicide tolerance.

In conclusion, the MTHFR66 protein of the present invention can degrade a dicamba herbicide, and the optimized MTHFR66 gene uses preferred codons of maize and soybean, so that it is particularly suitable for expression in plants; the optimized MTHFR66 gene can confer better dicamba herbicide tolerance to transgenic plants; furthermore, the herbicide tolerant protein MTHFR66 of the present invention further has methyltetrahydrofolate reductase activity, and is different from the known dicamba tolerant gene, and therefore it is possible to expand the application scope of dicamba tolerance in plants.

Finally, it should be stated that the above embodiments are merely used for illustrating rather than limiting the technical solution of the present invention; and although the present invention has been described in detail with reference to the preferred embodiments, a person skilled in the art should understand that modifications or equivalent substitutions may be made to the technical solution of the present invention without departing from the spirit and scope of the technical solution of the present invention.

The invention claimed is:

1. A gene, wherein the gene comprises:
   (a) the nucleotide sequence shown as SEQ ID NO: 1; or
   (b) a nucleotide sequence complementary to the nucleotide sequence defined in (a).

2. An expression cassette, wherein the expression cassette comprises the gene of claim 1 under the regulation of an effectively linked regulatory sequence.

3. A recombinant vector, comprising the gene of claim 1.

4. A method for extending the tolerance of a plant to herbicides, wherein the method comprises: expressing in the plant a first protein encoded by a gene comprising the nucleotide sequence shown as SEQ ID NO:1 or a first protein encoded by the expression cassette of claim 2 in a plant together with at least one second protein which is different from the first protein.

5. A method for selecting transformed plant cells, wherein the method comprises: transforming a plurality of plant cells with a gene comprising the nucleotide sequence shown as SEQ ID NO: 1 or the expression cassette of claim 2, and cultivating the cells under a concentration of herbicide allowing the growth of the transformed cells expressing the gene or the expression cassette, while killing the untransformed cells or inhibiting the growth of the untransformed cells, wherein the herbicide is dicamba.

6. A method for weed control, wherein the method comprises:
   applying an effective dose of a dicamba herbicide to a field for planting a plant, the plant containing a gene comprising the nucleotide sequence shown as SEQ ID NO: 1 or the expression cassette of claim 2.

7. A method for protecting a plant from damages caused by herbicides, wherein the method comprises: introducing a gene comprising the nucleotide sequence shown as SEQ ID NO: 1 or the expression cassette of claim 2 into a plant to make the resultant plant produce a sufficient amount of herbicide tolerant proteins for protecting the plant from damages caused by dicamba.

8. A method for conferring the dicamba herbicide tolerance to a plant, wherein the method comprises: introducing a gene comprising the nucleotide sequence shown as SEQ ID NO: 1 or the expression cassette of claim 2.

9. A method for controlling glyphosate tolerant weeds in a field for a glyphosate tolerant plant, wherein the method comprises: applying an effective dose of dicamba to a field for planting a glyphosate tolerant plant, the glyphosate tolerant plant containing a gene comprising the nucleotide sequence shown as SEQ ID NO: 1 or the expression cassette of claim 2.

10. A method for producing a dicamba tolerant plant, wherein the method comprises: introducing a gene comprising the nucleotide sequence shown as SEQ ID NO: 1 or the expression cassette of claim 2 into the genome of the plant to produce the dicamba tolerant plant.

11. The method for producing a dicamba tolerant plant according to claim 10, wherein the method comprises: producing a dicamba tolerant plant by selfing of a parent plant or hybridizing a parent plant with a second plant, the parent plant and/or the second plant containing a gene comprising the nucleotide sequence shown as SEQ ID NO: 1 or an expression cassette comprising a nucleotide sequence shown as SEQ ID NO: 1 under the regulation of an effectively linked regulatory sequence, and the dicamba tolerant plant inheriting the gene or the expression cassette from the parent plant and/or the second plant.

12. A method for cultivating a plant tolerant to a dicamba herbicide, wherein the method comprises:
   planting at least one plant seed, the genome of which containing a gene comprising the nucleotide sequence shown as SEQ ID NO: 1 or the expression cassette of claim 2;
   growing the plant seed into a plant;
   and spraying the plant with an effective dose of the dicamba herbicide, and harvesting a plant having a reduced plant damage compared to other plants without the gene or the expression cassette.

13. The method according to claim 4, wherein the plant is soybean, cotton, maize, rice, wheat, beet or sugar cane.

14. A recombinant vector, comprising the expression cassette of claim 2.

15. A method for weed control, wherein the method comprises: applying an effective dose of a dicamba herbicide to a field for planting a plant, the plant containing the recombinant vector of claim 3.

16. A method for protecting a plant from damages caused by herbicides, wherein the method comprises: introducing the recombinant vector of claim 3 into a plant to make the resultant plant produce a sufficient amount of herbicide tolerant proteins for protecting the plant from damages caused by dicamba.

17. A method for conferring the dicamba herbicide tolerance to a plant, wherein the method comprises: introducing the recombinant vector of claim 3 into a plant.

18. A method for controlling glyphosate tolerant weeds in a field for a glyphosate tolerant plant, wherein the method comprises: applying an effective dose of dicamba to a field for planting a glyphosate tolerant plant, the glyphosate tolerant plant containing the recombinant vector of claim 3.

* * * * *